United States Patent [19]

Barta et al.

[11] Patent Number: 5,451,679

[45] Date of Patent: Sep. 19, 1995

[54] 2-CHLORO AND 2-BROMO DERIVATIVES OF 1,5-IMINOSUGARS

[75] Inventors: Thomas E. Barta, Evanston; Richard A. Mueller, Glencoe, both of Ill.

[73] Assignee: G. D. Searle & Co., Skokie, Ill.

[21] Appl. No.: 207,340

[22] Filed: Mar. 8, 1994

[51] Int. Cl.$^6$ ............................................. C07D 211/40
[52] U.S. Cl. ..................................... 546/219; 546/220
[58] Field of Search ................................. 546/219, 220

[56] References Cited

U.S. PATENT DOCUMENTS

| | | | |
|---|---|---|---|
| 4,849,430 | 7/1989 | Fleet et al. | 514/315 |
| 5,003,072 | 3/1991 | Partis et al. | 546/243 |
| 5,025,021 | 6/1991 | Getman et al. | 514/302 |
| 5,030,638 | 7/1991 | Partis et al. | 514/315 |
| 5,206,251 | 4/1993 | Khanna et al. | 514/315 |
| 5,258,518 | 11/1993 | Khanna et al. | 546/242 |
| 5,268,482 | 12/1993 | Koszyk et al. | 546/242 |

OTHER PUBLICATIONS

Furneaux et al., Tetrahedron, vol. 50, No. 7, pp. 2131–2160 (1994).
Fleet et al., FEBS Lett. 237, 128–132 (1988).

*Primary Examiner*—C. Warren Ivy
*Assistant Examiner*—Raymond Covington
*Attorney, Agent, or Firm*—Scott J. Meyer

[57] ABSTRACT

Novel 2-chloro and 2-bromo derivatives of 1,5-iminosugars are disclosed, especially such derivatives of 1,5-dideoxy-1,5-imino-D-glucitol. These compounds are useful inhibitors of glucosidase enzymes and also are useful as antiviral agents and as intermediates for the synthesis of other enzyme inhibitors and antiviral compounds.

33 Claims, No Drawings

2-CHLORO AND 2-BROMO DERIVATIVES OF 1,5-IMINOSUGARS

BACKGROUND OF THE INVENTION

This invention relates to novel derivatives of 1,5-dideoxy-1,5-imino-D-glucitol having chloro or bromo substituents at C-2, and, more particularly, to the chemical synthesis of these derivatives and intermediates therefor. These compounds are useful for inhibiting glycosidase enzymes such as, for example, $\alpha$- and $\beta$-glucosidases.

1,5-dideoxy-1,5-imino-D-glucitol (deoxynojirimycin or DNJ) and its N-alkyl and O-acylated derivatives are known inhibitors of glycosidase enzymes. They are also known to be inhibitors of viruses such as human immunodeficiency virus (HIV) or pro-drugs for such inhibitors. See, e.g., U.S. Pat. Nos. 4,849,430; 5,003,072; 5,030,638 and PCT Int'l. Appln. WO 87/03903. Several of these derivatives also are effective against other viruses such as HSV and CMV as disclosed in U.S. Pat. No. 4,957,926. In some cases antiviral activity is enhanced by combination of the DNJ derivative with other antiviral agents such as AZT as described in U.S. Pat. No. 5,011,829. Various of these DNJ derivative compounds are reported to be antihyperglycemics and similar such therapeutic agents for metabolic diseases based on their activity as glycosidase inhibitors. See, e.g., U.S. Pat. Nos. 4,182,763, 4,533,668 and 4,639,436. Various 2-fluoro derivatives of 1,5-dideoxy-1,5-imino-D-glucitol have been described as glycosidase inhibitors in U.S. Pat. No. 5,025,021.

Further background information on the conventional use of DNJ and various related compounds as inhibitors of oligosaccharide processing, protein glycosylation and glycoprotein processing can be had by reference to leading review articles such as Truscheit et al., *Angew. Chem. Ind. Engl.* 20, 744–761 (1981); Elbein, *Crit. Rev. Biochem.* 16, 21–49 (1984); Fuhrmann et al., *Biochim. Biophys. Acta* 825, 95–100 (1985); Fellows, *Pestic. Sci.* 17, 602–606 (1986); Datema et al., *Pharmac. Ther.* 33, 221–286 (1987); and references cited therein.

Notwithstanding the foregoing, the search continues for the discovery and novel synthesis of new and improved glycosidase inhibitors.

BRIEF DESCRIPTION OF THE INVENTION

In accordance with the present invention, novel derivatives of 1,5-dideoxy-1,5-imino-D-glucitol (deoxynojirimycin or DNJ) having chloro or bromo substituents at C-2 are provided. These novel DNJ derivative compounds and various of their intermediates are useful inhibitors of glycosidase enzymes such as, for example, $\alpha$- and $\beta$-glucosidases, as demonstrated herein. They are thus useful in a great variety of commercial applications including, for example, enzyme assays, enzyme cultures and the regulation of enzyme catalytic process reactions. They also have useful antiviral activity as demonstrated herein against lentivirus. Compounds of this invention are also useful intermediates for the synthesis of other enzyme inhibitors and antiviral compounds. According to another embodiment of the invention, novel methods of chemical synthesis of these compounds and their intermediates are provided.

The novel C-2 chloro and bromo substituted derivatives of 1,5-dideoxy-1,5-imino-D-glucitol can be represented by the following general structural Formula I.

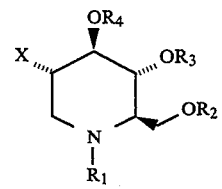

In Formula I, X is Cl or Br; $R_1$ is H or a $C_1$–$C_{12}$ branched or unbranched alkyl group, alkoxyalkyl, alkenyl, alkynyl, arylalkyl, substituted arylalkyl, arylalkenyl or substituted arylalkenyl; and $R_2$, $R_3$ and $R_4$ are independently H or $COR_5$ where $R_5$ is $C_1$–$C_6$ branched or unbranched alkyl, or $C_6$–$C_{12}$ aryl or alkylaryl.

The $R_1$ groups preferably are alkyl groups such as methyl, ethyl, propyl, n-butyl, (2-ethyl)butyl, pentyl, hexyl, heptyl, octyl, nonyl, decyl, undecyl, dodecyl and the like; alkoxyalkyl groups such as (2-methoxy)butyl, ethoxypropyl, propoxypropyl and the like; arylalkyl groups such as phenylmethyl, phenylethyl, (3-phenyl)propyl and the like; and substituted arylalkyl groups such as (4-methoxyphenyl)methyl, (4-ethoxyphenyl)ethyl, (4-propoxyphenyl)methyl and other such arylalkyl groups substituted with halogen such as Cl, Br or F, nitro and hydroxyl.

The $R_2$, $R_3$ and $R_4$ groups preferably are H or alkanoyl groups such as acetyl, propionyl, butyryl and valeryl.

The $R_5$ groups preferably are alkyl groups such as methyl, ethyl, propyl, n-butyl, (2-ethyl)butyl, pentyl and hexyl; aryl groups such as phenyl and benzyl; and arylalkyl groups such as phenylmethyl, phenylethyl, (3-phenyl)propyl and the like.

Useful novel intermediates include compounds similar to the compounds of Formula I in which the primary hydroxyl (C-6) is protected with $Si(R_6R_7R_8)$, preferably with a t-butyldiphenylsilyl group. Other novel intermediates for synthesizing compounds of Formula I are deoxynojirimycin derivatives having a 2,3-O-(di-n-butylstannylene) protecting group or an epoxy group at C-2, C-3 and in which the C-6 hydroxyl is optionally protected with $Si(R_6R_7R_8)$.

Still other novel compounds made in conjunction with the foregoing compounds are non-halo sugars of the following general structural Formula II.

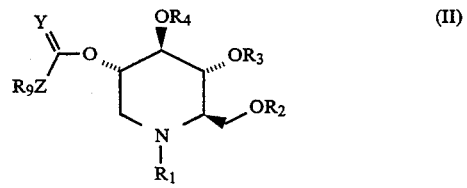

In Formula II, Y is O or S; Z is NH or O; $R_1$ and $R_2$, $R_3$ and $R_4$ are defined as in general structural Formula I, above. $R_6$, $R_7$ and $R_8$ are independently $C_1$–$C_6$ branched or unbranched alkyl, or $C_6$–$C_{12}$ aryl or alkylaryl. $R_9$ is a $C_1$–$C_{12}$ branched or unbranched alkyl or $C_6$–$C_{12}$ aryl or alkylaryl. The compounds of Formula II preferably have substituents at C-2 such as (2-methylpropyl)carbonate, phenylcarbamoate and butylcarbamoate. These compounds can be prepared from the same intermediate deoxynojirimycin derivatives having a 2,3-O-(di-n-butylstannylene) protecting group at C-2, C-3 which are used for synthesizing compounds of Formula I.

In accordance with another embodiment of the invention, novel compounds of the structure of Formula I can be used for the further synthesis of 5-membered ring compounds of the following general structural Formula III:

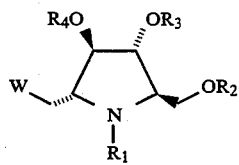

In Formula III, $R_1$, $R_2$, $R_3$ and $R_4$ are defined as in the general structural Formulas I and II but can also be aroyl groups, e.g., benzoate groups; provided, however, that when W is OH, $R_2$ is not H. W is defined as Cl, Br, CN, $N_3$, SCN, OH, $R_5(CO)O$—, $R_5(CO)S$—, $R_5(CS)S$—, $(NR_9R_{10})(CO)O$—, $(NR_9R_{10})(CS)O$—, $R_{10}R_{11}N$—, $R_9S$—, $R_9SO$—, $R_9SO_2$—, HetS—, HetSO—, $HetSO_2$, Het. $R_9$ is defined as in general structural formula II. $R_{10}$ and $R_{11}$ are independently H or $R_9$; provided, however, that when the $R_9$ in $R_9SO$ or $R_9$ in $R_9SO_2$ is H, the oxidation products are sulfinic or sulfonic acids and not sulfoxides or sulfones. Het is a substituted or unsubstituted 5 or 6 membered aromatic heterocyclic ring containing 1 to 4 nitrogen, oxygen or sulfur heteroatoms. The heterocyclic ring may be fused to a benzene ring. Examples of heterocyclic rings include imidazoles, pyrazoles, pyrroles, thiazoles, thiadiazoles, thiophenes, tetrazoles, thiazoles, thiophenes, furanes, oxazoles, pyrimidine, triazine, benzoxazole, ozadiazol, pyridines, pyrazines, indoles, benzofuranes, benzothiophenes, benzothiazoles, benzimidazoles and the like.

Preferred compounds of Formula I are the following:
1,5-(Butylimino)-2-chloro-1,2,5-trideoxy-D-glucitol
2-Chloro-1,2,5-trideoxy-1,5-(hexylimino)-D-glucitol
2-Chloro-1,2,5-trideoxy-1,5-(nonylimino)-D-glucitol
2-Chloro-1,2,5-trideoxy-1,5-(3-phenyl)-propylimino-D-glucitol
2-Chloro-1,2,5-trideoxy-1,5-(2-ethyl)-butylimino-D-glucitol
2-Chloro-1,2,5-trideoxy-1,5-(phenylmethyl)-imino-D-glucitol
2-Chloro-1,2,5-trideoxy-1,5-[(4-methoxyphenyl)-methyl-imino]-D-glucitol
1,5-(Butylimino)-2-chloro-1,2,5-trideoxy-D-glucitol, triacetate
2-Chloro-1,2,5-trideoxy-1,5-(3-phenyl)-propylimino-D-glucitol, triacetate
1,5-(Butylimino)-2-chloro-1,2,5-trideoxy-D-glucitol, tributyrate
2-Bromo-1,5-butylimino-1,2,5-trideoxy-D-glucitol, triacetate Preferred compounds of Formula II are the following:
1,5-( Butylimino)-1,5-dideoxy-D-glucitol, 2-[(2-methylpropyl)carbonate]
1,5-( Butylimino)-1,5-dideoxy-D-glucitol, 2-(phenylcarbamoate)
1,5-( Butylimino)-1,5-dideoxy)-D-glucitol, 2-(butylcarbamoate)

Preferred compounds of Formula III are the following:

1-Azido-2,5-(butylimino)-1,2,5-trideoxy-D-mannitol
1-Amino-2,5-(butylimino)-1,2,5-trideoxy-D-mannitol
2,5-(Butylimino)-1-(dibutylamino)-1,2,5-trideoxy-D-mannitol
1-(Acetylamino)-2,5-(butylimino)-1,2,5-trideoxy-D-mannitol
3,6-(Butylimino)-2,3-6-trideoxy-D-manno-heptanonitrile
2,5-(Butylimino)-2,5-dideoxy-1S-(1-methyl-1H-tetrazol-5-yl)-1-thio-D-mannitol
2,5-(Butylimino)-2,5-dideoxy-D-mannitol, 1-benzoate It will be understood that pharmaceutically acceptable salts of the foregoing compounds are also included within the scope of the invention such as, e.g. salts of organic and inorganic acids. These salts can be formed by conventional methods known in the art such as by reaction of the base compound with an appropriate acid, e.g. HCl and the like.

The novel synthesis of compounds of Formula I comprises the formation of structural modifications for introduction of a chloro or bromo substituent at C2.

The novel compounds of the invention as defined by Formulas I, II and III, above, can be prepared by various reactions as illustrated by the following general reaction schemes.

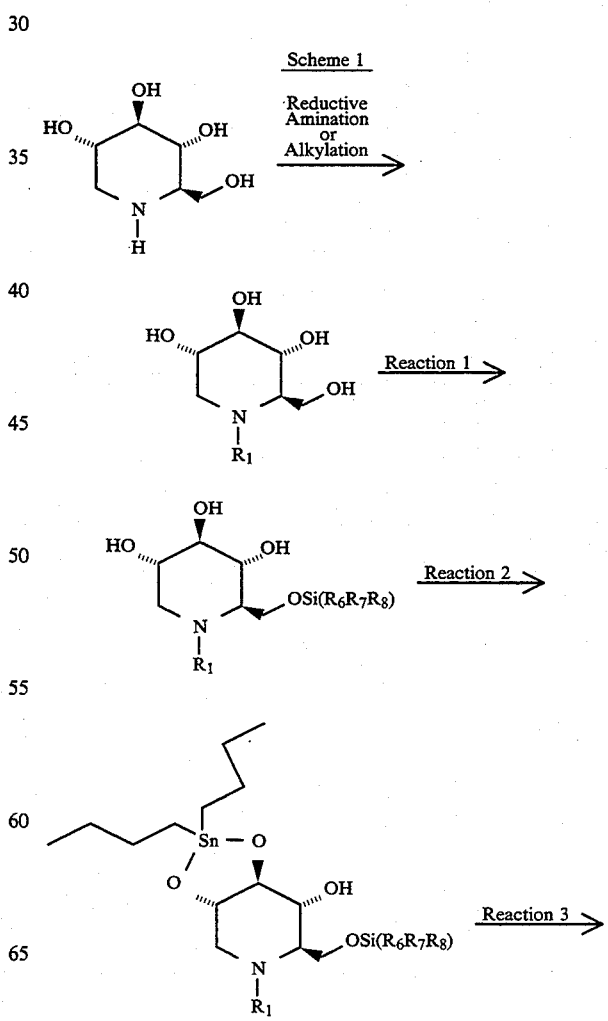

5,451,679
5
-continued
Scheme 1
6
-continued
Scheme 2
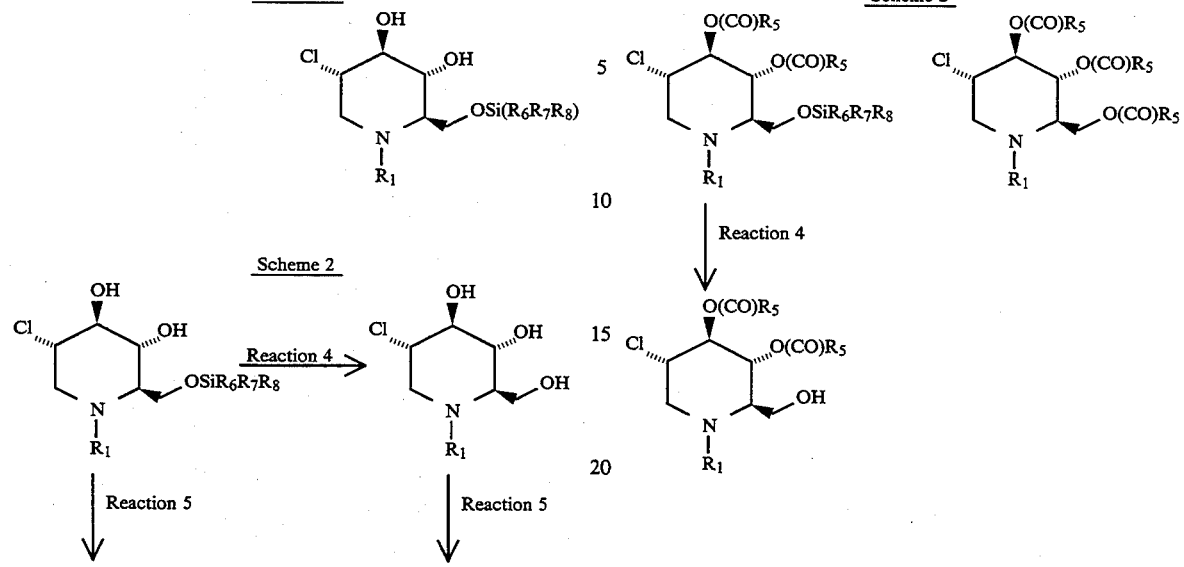
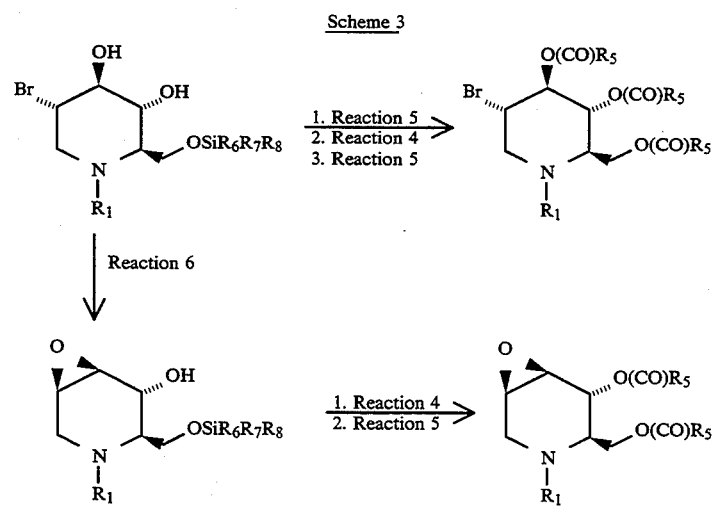
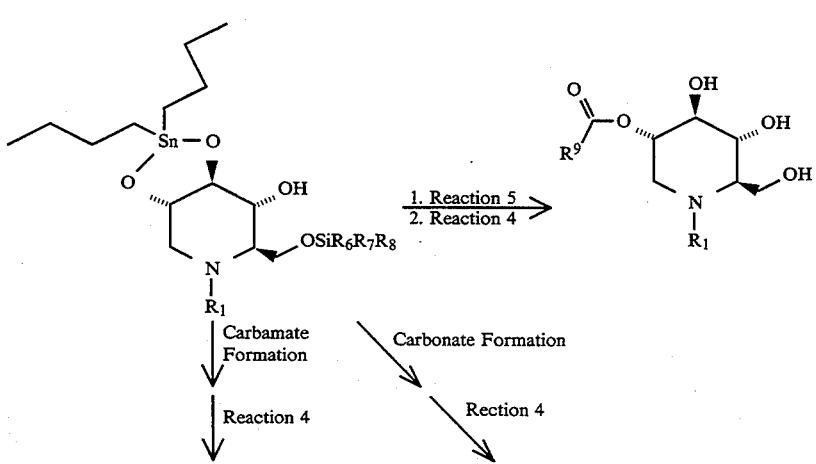

5,451,679
-continued
Scheme 4
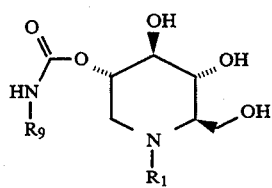 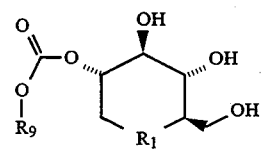
Scheme 5
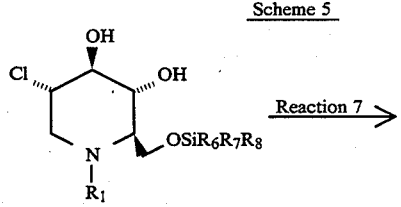
-continued
Scheme 5
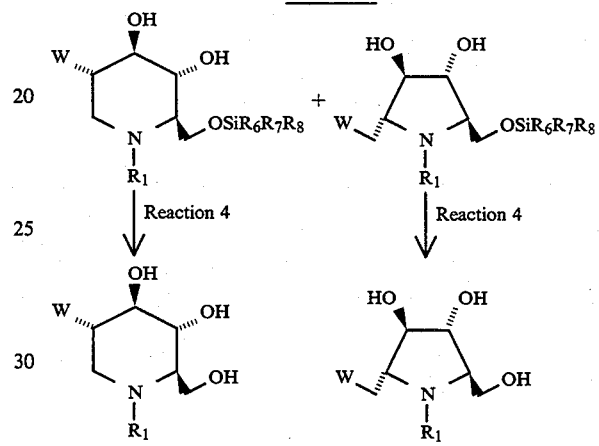
Scheme 6
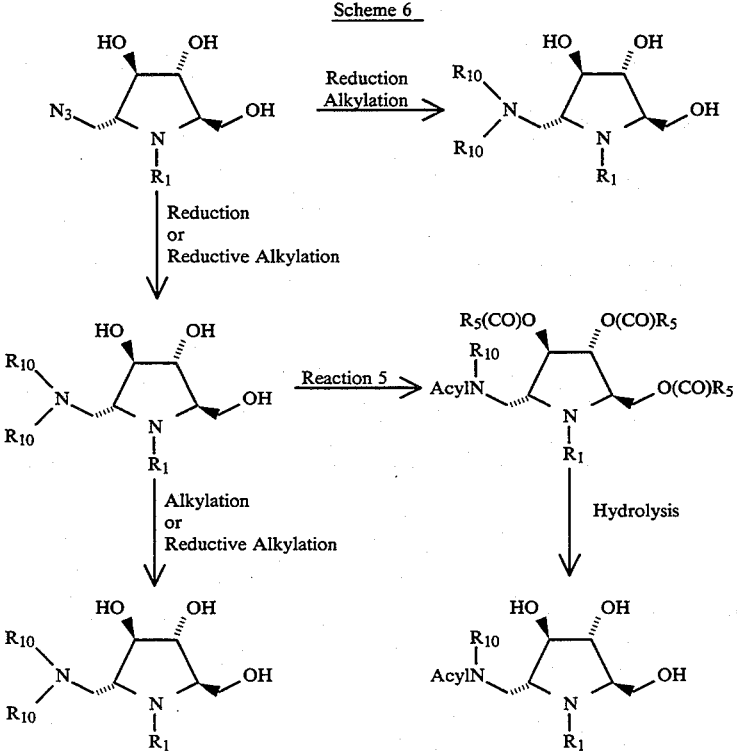

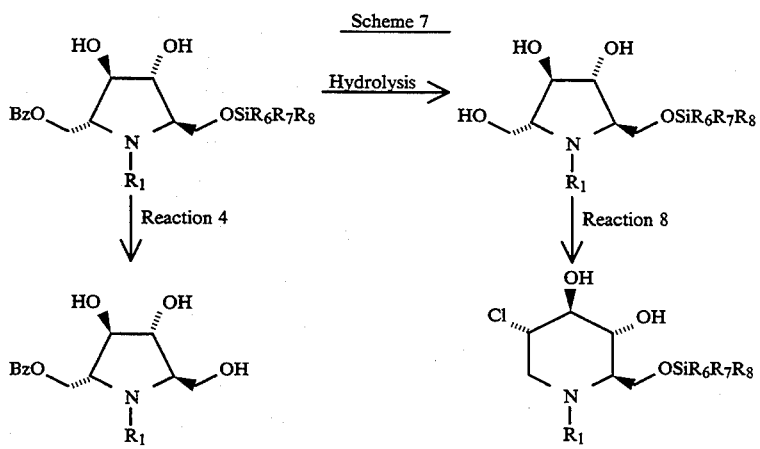

Scheme 7

N-substituted derivatives of deoxynojirimycin which are used as starting materials in the foregoing reaction scheme 1 are known compounds as disclosed hereinbefore. They can be prepared in a preliminary reaction step by conventional reductive amination or alkylation of deoxynojirimycin.

For the silylation step (reaction 1) to protect the primary hydroxyl with $Si(R_6R_7R_8)$, the preferred conditions include use of t-butyldiphenylsilyl chloride (0.9–1.15 molar equivalents), with catalytic N,N-dimethylamino-pyridine (1-20 mole percent), and employment of triethylamine or diisopropylethylamine as base, in N,N-dimethylformamide or acetonitrile, at temperatures of 0°–30° C. See also illustrative Examples 1–7.

Formation of the cyclic stannylene (reaction 2) is accomplished by using dibutyltin oxide (0.95–1.05 molar equivalents) as the preferred reagent in methanol or ethanol (0.1–0.25M) at ambient temperature to reflux temperature. See also illustrative Examples 8–14.

Toluenesulfonyl chloride or bromide (0.95–1.15 molar equivalents) are preferred reagents for reaction 3. The reaction is run preferably in solvents such as dichloromethane and tetrahydrofuran (0.05–0.50M), using triethylamine or diisopropylethylamine (0.95–1.15 equivalents) as the base, at temperatures from 0°–30° C. See also illustrative Examples 15–21.

Removal of the silyl protecting group (reaction 4) is done preferentially at 0°–30° C. in methanol or ethanol (0.1–1.0M) using 1–10 molar equivalents of $KHF_2$ or HF/pyridine. See also illustrative Examples 27–37.

Acylation (reaction 5) of the free hydroxyls with $COR_5$ is run preferably at 0°–25° C., in dichloromethane, tetrahydrofuran, or acetonitrile, using as base triethylamine, diisopropylethylamine, or pyridine. See also illustrative Examples 38–40.

Epoxidation at C-2, C-3 (reaction 6) is run preferably in dichloromethane or tetrahydrofuran, using 0.95–1.2 molar equivalents 1,5-diazabicyclo-[4.3.0]non-5-ene or 1,8-diazabicyclo[5.4.0]-undec-7-ene as base at a temperature of 0°–25° C. See also illustrative Example 42.

For the displacement of halide at C-2 to give 5- and 6-membered products (reaction 7), N,N-dimethylformamide and acetonitrile are preferred solvents. 1–5 molar equivalents of nucleophile is typically employed, with preference for sodium salts. Preferred temperatures range from 20°–82° C. See also illustrative Examples 46, 52 and 55.

Toluenesulfonyl chloride or bromide are preferred reagents for reaction 8. The reaction is run preferably in solvents such as dichloromethane and tetrahydrofuran, using triethylamine or diisopropylethylamine as the base and catalytic N,N-dimethylaminopyridine (0–15 mole percent), at temperatures from 0°–30° C. See also illustrative Example 60.

Although the foregoing reaction schemes set forth preferred reagents and conditions, it will be appreciated that, in general, one skilled in the art can readily replace components mentioned in these schemes with alternate reagents under substantially equivalent conditions. For example, one can use various non-protic or dipolar aprotic solvents such as xylene, dimethoxyethane, diethoxyethane, sulfolane, dimethylformamide, dimethylsulfoxide, dioxane, furan, thiophene, dimethyacetamide, heptane, tetramethylurea and the like. Alternative protic solvents include methanol, water, isopropanol, tert-butanol, ethoxyethanol and the like which may replace the exemplified protic solvents when the solvent is not also used as a specific reagent. The preferred temperature for the reactions disclosed in the schemes and examples is room temperature unless otherwise specified, however, in some cases temperatures between −78° C. and solvent reflux may be used. Many examples disclosed herein require a dry atmosphere to obtain the best results or for safety reasons. An inert atmosphere may also be used such as that obtained using an atmosphere of argon or nitrogen. Alternative non-reagent amine bases include, for example, N-methylmorpholine, diaza-bicyclononane, N,N-dimethylaminopyridine (DMAP) and the like. Mineral bases can include sodium carbonate, sodium bicarbonate, potassium hydroxide, sodium hydroxide, lithium hydroxide, lithium carbonate, calcium carbonate, barium hydroxide and aluminium hydroxide or oxide. Hydride bases can include lithium hydride, calcium hydride, potassium hydride and the like as well as organometallic bases such as tert-butyl lithium, lithium acetylide, ethyl magnesium bromide, isopropyl magnesium chloride and the like. Other useful acids can include, for example, hydrogen bromide, hydrobromic acid, sulfuric acid, phosphoric acid, potassium phosphate, toluenesulfonic acid, benzenesulfonic acid, methanesulfonic acid, benzyl phosphoric acid, trifluoromethyl sulfonic acid, nitrobenzoic acid, trichloroacetic acid and acetic acid as well as Lewis acids such as aluminum chloride, boron trifluoride, tin chlorides, titanium halides and the like. Hydrogenation catalysts can include, for example, palladium chloride, palladium metal of various mesh sizes, palladium on barium sulfate, nickel, platinum and platinum oxide with hydrogen gas as well as with hydrogen transfer molecules such as cyclohexadiene and cyclohexene used with or without pressures greater than atmospheric pressure.

In carrying out the silylation in reaction 1 (Scheme 1), alternatives to t-butyldiphenylsilyl chloride include, for example, t-butyldiphenylsilyl bromide, t-butyldiphenylsilyl iodide, t-butyldiphenylsilyl imidazole, t-butyldiphenylsilyl triflate and t-butyldimethylsilyl chloride. Triisopropylsilyl chloride, triphenylsilyl chloride, dimethylhexylsilyl chloride represent examples of reagents that can be used to obtain substituted silyl derivatives. Alternative hydroxyl protecting groups that can be used for selective derivatization of the 6-hydroxyl are triphenylmethyl chloride, triarylmethyl halides (e.g.,tri-para-methoxyphenylmethyl bromide), and adamantanecarbonyl chloride, as well as polymer-supported versions of the above reagents. Suitable solvents include, for example, N,N-dimethylformamide, 2,6-lutidine, and hexamethylphosphoramide. Alternative bases include diisopropylethylamine, N,N-dimethylaniline, imidazole, 2,6-lutidine and 1,8-diazabicyclo[5.4.0]-undec-7-ene. 4-Dimethylaminopyridine can be used in amounts varying from catalytic amounts in combination with another base up to about one molar equivalent. Temperatures suitable for silylation extend from about 0° C. to about 100° C. A dry atmosphere, such as argon or nitrogen, is preferred.

Reaction 2 in Scheme 1 illustrates the preparation of a cyclic tin derivative. One can substitute, for example, dimethyltin oxide, tetramethylenetin oxide, or diphenyltin oxide for di-n-butyltin oxide in this step to obtain the corresponding analog. Other alcohols, such as ethanol, isopropanol, methoxyethanol can be used as pure or mixed solvents. Concentration can be widely varied over several orders of magnitude. The reaction can be run at temperatures from about −20° C. to about 150° C. or the boiling point of solvent(s). A dry, inert atmosphere, such as argon or nitrogen, is preferred.

The cyclic tin derivatives prepared according to reaction 2 in Scheme I not only are useful as intermediates for preparing the halo-sugars of this invention as defined in general structural Formula I, but also are useful as intermediate in the production of non-halo sugars of general structural Formula II as illustrated by reaction 4 of Scheme 4.

Reaction 3 (Scheme 1) represents a novel step in the method of preparing the halo-sugars of this invention. Alternatives to toluenesulfonyl chloride or bromide include methanesulfonyl chloride, nitrophenyl-sulfonyl chloride, methoxyphenylsulfonyl chloride, napthylsulfonyl chloride, sulfuryl chloride, thionyl chloride and the like. Reagents other than sulfonyl halides can be reacted with the cyclic stannylene species to afford other novel chemical species which do not incorporate halide (Scheme 4). Such reagents include acyl chlorides and anhydrides ($R_9(CO)Cl$ and $R_9(CO)O(CO)R_9$), chloroformates ($R_9(CO)Cl$), isocyanates ($R_9NCO$) and sulfur-containing versions of the aforesaid compounds (e.g., isothiocyanates ($R_9NCS$) and thiochloroformates ($R_9S(CO)Cl$), in which $R_9$ can be groups such as defined above for $R_1$ and $R_5$. Suitable solvents include, for example, acetonitrile, chloroform, tetrahydrofuran, nitrobenzene, anisole, and pyridine, as pure solvents or as a mixed system. Alternative bases can be diisopropylethylamine, N,N-dimethylaniline, pyridine, 2,6-lutidine, and 1,8-diazabicyclo[5.4.0]undec-7-ene and the like. Various reactions can be run in the absence of base. Concentration of reagents can be varied over several orders of magnitude (e.g, from about 0.01M to about 2.0M). Temperatures between about −40° C. and about 80° C. are suitable. A dry, inert atmosphere, such as argon or nitrogen, is preferred.

Reaction 4 (Schemes 2, 3, 4, and 7), the desilylation, can be carried out with other reagent systems, such as triethylamine-HF, pyridine-HF, polyvinylpyridine-HF, tetrabutylammonium fluoride, or CsF in amounts ranging from about one to about 100 molar equivalents in solvents such as methanol, ethanol, aqueous tetrahydrofuran, acetonitrile, or acetone and the like. Alternatively, acidic reagents such as acetic acid or hydrochloric acid in methanol can be employed. Concentration of reagents can be varied over several orders of magnitude (e.g, from about 0.01M to about 2.0M). Temperatures suitable for desilylation extend from about −40° C. to about 50° C.

Reaction 5 (Schemes 2 and 3), acylation, can be achieved using a broad variety of reagents, including acyl chloride, acyl bromide, acyl anhydride, mixed anhydrides or similar reagents ($R_5(CO)O(CO)R_5$). As solvent, one can use non-protic or dipolar aprotic solvents such as xylene, dimethoxyethane, diethoxyethane, sulfolane, dimethyl-formamide, dimethylsulfoxide, dioxane, furan, thiophene, dimethyacetamide, heptane, tetramethylurea and the like. Bases such as pyridine, N,N-dimethylaniline, and triethylamine can be employed, at temperatures ranging from about −40° C. to about 50° C. and concentrations ranging from about 0.01M to about 2.0M. A dry, inert atmosphere, such as argon or nitrogen, is preferred.

In reaction 6 (Scheme 3), epoxide formation, a suitable alternative base can be 1,5-diazabicyclo-[4.3.0]non-5-ene. Other bases include amine bases such as triethylamine, hydride bases such as sodium hydride, and amide bases such as lithium hexamethyldisilazane. Various solvent systems are acceptable, including phenyl cyanide, toluene, and tetrahydrofuran. Concentration of reagents can be varied over several orders of magnitude. Temperature can be varied from about −40° C. to about 50° C. A dry, inert atmosphere, such as argon or nitrogen, is preferred.

In the nucleophilic displacement, reaction 7 (Scheme 5), alternative solvents include: 2-butanone, N,N-dimethylformamide, hexamethylphosphoramide, nitrobenzene, and the like, or mixtures thereof. Additives such as 18-crown-6 can be employed. Concentration of reagents can be varied over several orders of magnitude (e.g. from about 0.01M to about 2.0M). Temperature could be varied from about −20° to about 160° C. Illustrative examples of other suitable nucleophiles include potassium azide; lithium azide; tetrabutylammonium azide; sodium formate; sodium pivaloate; N,N-dibenzylglycine, sodium salt; sodium 2,2,2-trifluoroethylate; sodium thiobenzoate; thiourea; sodium thiophenylate; sodium thiophosphate; sodium thiocyanate; sodium 4-fluorophenylate; 1H-tetrazole, sodium salt; 2-mercapto-1-methylimidazole, sodium salt; 3-mercapto-4-methyl-4H-1,2,4-triazole, sodium salt; 2-mercaptobenzoxazole, sodium salt; 2-mercaptopyrimidine, sodium salt; 2-mercaptopyridine, sodium salt; 2-mercaptopyridine N-oxide, sodium salt; sodium phthalimide; sodium saccharin; sodium ascorbate; sodium tetronate; and fluorouracil, sodium salt. Displacement of a halogen atom in a compound having the structure of Formulas I or III can. also be accomplished with other choices of nucleophiles such as heterocycles with nucleophilic atoms in their rings as well as those with nucleophilic groups attached to side chains. In addition, thiols or thiolate salts are also effective nucleophiles as is well known to those skilled in the art. In cases where a heterocyclic quaternary ammonium salt is formed, it can be reduced with hydride reagents such as sodium borohydride, sodium cyanoborohydride, borane, lithium aluminum hydride, aluminum hydride and the like or by hydrogenation with a metal catalyst. Difunctional nucleophiles, such as terephthalic acid, disodium salt can also be employed, as can isotopically enriched species, such as Na$^{13}$CN. A dry, inert atmosphere, such as argon or nitrogen, is preferred. It is understood that several transformations listed above (e.g. reactions 7, 4, and 5) can be carried out by one skilled in the art sequentially, in a one-pot process.

For reaction 8 (Scheme 7), conversion of the 5-membered ring amino sugars into 6-membered ring amino sugars, alternatives to toluenesulfonyl chloride include methanesulfonyl chloride, nitrophenylsulfonyl chloride, methoxyphenylsulfonyl chloride, napthylsulfonyl chloride, sulfuryl chloride, thionyl chloride and the like. Analogous chemistry can be performed using toluenesulfonyl bromide and a similar aziridine or aziridinium intermediate is believed to be involved. Suitable solvents include acetonitrile, chloroform, tetrahydrofuran, nitrobenzene, anisole, and pyridine, as pure solvents or as a mixed system. Alternative bases are diisopropylethylamine, N,N-dimethylaniline, pyridine, 2,6-lutidine, and 1,8-diazabicyclo-[5.4.0]undec-7-ene. Concentration of reagents can be varied over several orders of magnitude (e.g, from about 0.01M to about 2.0M). Temperatures between about −40° C. and about 80° C. are suitable. A dry, inert atmosphere, such as argon or nitrogen, is preferred. It should be noted that this Scheme along with Scheme 5 illustrates the interconvertability and reversability of the reactions in this invention where one can select the product desired and recover or recycle valuable materials if desired.

Reductive alkylation or direct alkylation of, for example, a primary or secondary amine (Scheme 6), can be implemented by several methods that are well known in the art. Condensation of an aldehyde or ketone with the amine followed by or in conjunction with reduction is one such method. Suitable reducing agents are, for example, hydride transfer agents such as sodium cyanoborohydride or hydrogenations. Hydrogenations can use homogeneous or heterogeneous metal catalysts such as palladium, platinum, nickel, rhodium and the like.

Conversion of an azide (W=N$_3$) of this invention into the corresponding amine (W=NH$_2$) is shown in Scheme 6. A convenient method of reduction of this group is hydrogenation in the presence of a metal such as palladium, palladium on carbon, platinum, platinum oxide, rhodium and the like, either supported on an inert support such as carbon, silica, barium sulfate or as a complex such as with phosphine ligands. This process can also be combined with the reductive alkylation step to produce primary or secondary amine derivatives.

For synthesis of compounds in which R$_1$ is H, it is preferred to use a conventional protecting agent, e.g. BOC, on the ring nitrogen during synthesis which can be removed after the synthesis.

In standard biological tests, the novel compounds of this invention have been shown to have inhibitory activity against α- and β-glucosidase enzymes and also against lentiviruses such as visna virus and human immunodeficiency virus (HIV).

Inhibitory activity against α- and β-glucosidase enzymes was determined by conventional in vitro assays for these enzymes as described in U.S. Pat. No. 4,973,602. These assays involve spectrophotometric measurement of the release of p-nitrophenol from the substrate p-nitrophenyl-glycoside in the presence and absence of the test compound and comparison against a control standard that contains a known inhibitor of the enzyme.

Inhibitory activity against HIV-1 was shown by tests involving plating of susceptible human host cells which are syncytium-sensitive with and without virus in microculture plates, adding various concentrations of the test compound, incubating the plates for 7 to 9 days (during which time infected, non-drug treated control cells are largely or totally destroyed by the virus), and then determining the remaining number of viable cells with a colorometric endpoint.

Inhibitory activity against visna virus was shown by a conventional plaque reduction assay. Visna virus, a lentivirus genetically very similar to the AIDS virus, is pathogenic for sheep and goats. See Sonigo et al., *Cell* 42, 369–382 (1985); Haase, *Nature* 322, 130–136 (1986). Inhibition of visna virus replication in vitro as a useful model for HIV and its inhibition by test compounds has been described by Frank et al., *Antimicrobial Agents and Chemotherapy* 31(9), 1369–1374 (1987).

The novel 2-chloro derivatives of deoxynojirimycin of this invention have advantageous anti-viral properties that are not exhibited by the corresponding 2-fluoro derivatives of deoxynojirimycin. This is illustrated by a side-by-side comparison between the 2-chloro-N-butyl-DNJ of the present invention and the corresponding 2-fluoro-N-butyl-DNJ disclosed in U.S. Pat. No. 5,025,021. Thus, the 2-chloro derivative had a calculated (by linear regression) EC$_{50}$=43 μg/mL in a standard CEM cell assay for HIV inhibition (TD$_{50}$=187 μg/mL) with 62.5% inhibition at 100 μg/mL and 29.3% at 10 μg/mL, whereas the 2-fluoro derivative inhibited only 3% at 500 μg/mL, 0% at 100 μg/mL and 0% at 10 μg/mL. Moreover, the foregoing illustrative 2-chloro derivative also is a better enzyme inhibitor than the corresponding 2-fluoro derivative. The 2-chloro derivative inhibits α-glucosidase 46% and β-glucosidase 32% at 0.1 mM, whereas the corresponding 2-fluoro derivative inhibits these enzymes at only 8% and 4% at the same concentration according to U.S. Pat. No. 5,025,021.

DETAILED DESCRIPTION OF THE INVENTION

The following detailed Examples will further illustrate the invention although it will be understood that the invention is not limited to these specific Examples or the details described therein.

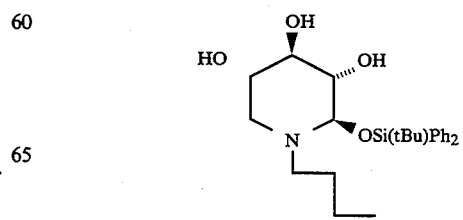

EXAMPLE 1

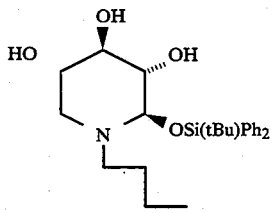

1,5- (Butylimino) -1,5-dideoxy-6-O- [(1,1-dimethyl)-diphenyl]-D-glucitol

To a stirred suspension of N-butyldeoxynojirimycin (6.02 g, 27.5 mMol) in N,N-dimethylformamide (27.5 mL), triethylamine (3.24 g) and N,N-dimethylaminopyridine (150 mg) were added. t-Butylchlorodiphenylsilane (7.97 g) was added and stirring was continued at ambient temperature for 1.5 hours. The mixture was diluted with ethyl acetate (300 mL) and extracted with water (300 mL). The aqueous phase was extracted with additional ethyl acetate (300 mL, followed by 20 mL) and the organic phases were combined, dried using magnesium sulfate, concentrated by rotary evaporation, and subjected to silica gel chromatography (95:5 ethyl acetate: methanol eluant). The combined product-containing functions were concentrated, diluted with solvent (ca. 10 mL), re-concentrated, and allowed to stand in vacuo. The title compound expanded into a solid white foam (11.10 g, 88%): mass spectrum, m/e 458 (MH+), $^1$H-NMR (CDCl$_3$): 7.70–7.66 (m, 4H); 7.49–7.38 (m, 6H); 3.98 (dd, 1H, J$_1$=10.5 Hz, J$_2$=4.0 HZ); 3.83 (br.s, 1H); 3.82 (dd, 1H, J$_1$=10.5 Hz, J$_2$=7.0 Hz); 3.64 (ddd, 1H, J$_1$=10.5 Hz, J$_2$=9.5 Hz, J$_3$=5.0 Hz); 3.55 (dd, 1H, J$_1$=9.5 Hz, J$_2$=9.0 Hz); 3.32 (t,1H); 2.96 (dd, 1H, J$_1$=11.0, J$_2$=5.0); 2.88 (br.s, 1H); 2.48 (ddd, 1H, J$_1$=12 Hz, J$_2$=10.0 Hz, J$_3$=6.0 Hz) 2.37 (ddd, 1H, J$_1$=9.0 Hz, J$_2$=7.0 Hz, J$_3$=4.0 Hz); 2.30 (ddd, 1H, J$_1$=12 Hz, J$_2$=9.5 Hz, J$_3$=5.0 Hz); 2.24 (dd, 1H, J$_1$=11 Hz, J$_2$=10.5 Hz); 1.54 (br.s, 1H); 1.34–0.99 (m, 4H); 1.06 (S, 9H); 0.78 (t, 3H, J=7.5 Hz)

Anal. calc. for C$_{26}$H$_{39}$NO$_4$Si: C, 68.23; H, 8.59; N, 3.06. Found: C, 68.08; H, 8.76; N, 3.00.

EXAMPLE 2

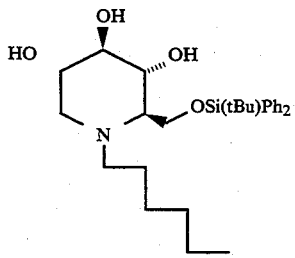

1,5-Dideoxy-6-O- [(1,1-dimethylethyl)diphenylsilyl ]-1,5-(hexylimino)-D-glucitol The title compound was prepared by the method of Example 1 using N-hexyldeoxynojirimycin (2.79 g) in the place of N-butyldeoxynojirimycin and proceeding in 81% yield. The structure was confirmed by NMR.

EXAMPLE 3

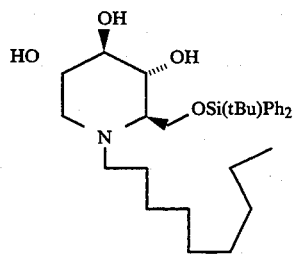

1,5-Dideoxy-6-O-[(1,1-dimethylethyl)diphenylsilyl]-1,5- (nonylimino)-D-glucitol

The title compound was prepared by the method of Example using N-nonyldeoxynojirimycin (1.78 g) in the place of N-butyldeoxynojirimycin and proceeding in 74% yield. The structure was confirmed by NMR.

EXAMPLE 4

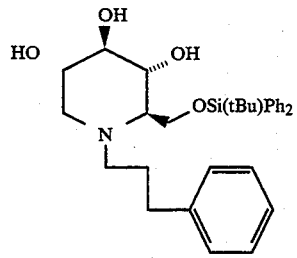

1,5-Dideoxy-6-O-[(1,1-dimethylethyl)diphenylsilyl]-1,5-(3-phenyl)propylimino-D-glucitol The title compound was prepared by the method of Example 1 using N-(3-phenyl)propyldeoxynojirimycin (2.89 g) in the place of N-butyldeoxynojirimycin and proceeding in 80% yield. The structure was confirmed by NMR.

EXAMPLE 5

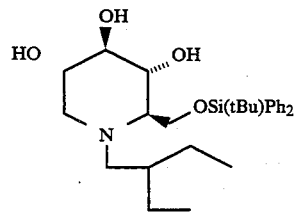

1,5-Dideoxy-6-O-[(1,1-dimethylethyl)diphenylsilyl]-1,5- (2-ethyl)butylimino-D-glucitol The title compound was prepared by the method of Example 1 using N-(2-ethyl)butyldeoxynojirimycin (0.696 g) in the place of N-butyldeoxynojirimycin and proceeding in 43% yield. The structure was confirmed by NMR.

EXAMPLE 6

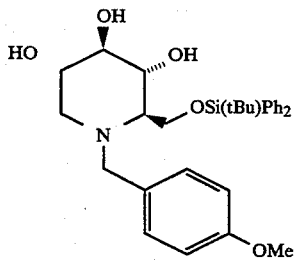

1,5-Dideoxy-6-O-[(1,1-dimethylethyl)diphenylsilyl]-1,5-(4-methoxyphenyl)methylimino-D-glucitol Deoxynojirimycin (1.63 g, 10.0 mmol) was suspended in N,N-dimethylformamide (30 mL). Diisopropylethylamine (2.97 g) and 4-methoxybenzyl chloride (1.96 g) were added, consecutively, and the stirred mixture was warmed to 52° C.±3° C. and maintained at that temperature overnight. The resulting homogeneous solution was cooled to ambient temperature whereupon t-butyldiphenylsilyl chloride (2.79 g) and N,N-dimethylaminopyridine (80 mg) were added. After 2 hours, the product mixture was diluted with ethyl acetate (200 mL) and washed with water (300 mL). The aqueous layer was extracted with additional ethyl acetate (2×100 mL), the organic layers were combined, and subsequently dried using magnesium sulfate. The solvent was removed by rotary evaporation. Chromatography followed by concentration in the presence of several mL toluene afforded the title compound as a white solid foam (3.00 g, 58%). The structure was confirmed by NMR.

EXAMPLE 7

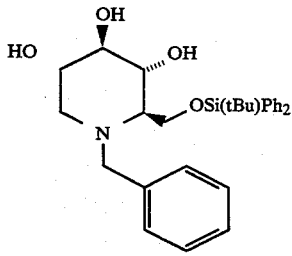

1,5-Dideoxy-6-O-[1,1-dimethylethyl)diphenylsilyl]-1,5-(phenylmethyl)imino-D-glucitol The title compound was prepared by the method of Example 6 using benzyl bromide in the place of 4-methoxybenzyl chloride. From 0.815 g (5 mmol) of deoxynojirimycin was obtained 1.97 g (80%) of the desired title compound. The structure of the product was confirmed by NMR.

EXAMPLE 8

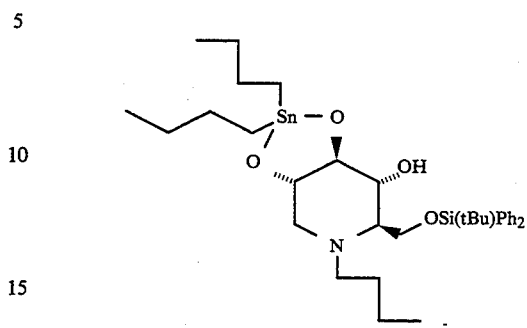

1,5-(Butylimino)-1,5-dideoxy-2,3-O-(dibutylstannylene)-6-O-[(1,1-dimethylethyl)diphenylsilyl]-D-glucitol The title compound of Example 1, 1,5-(butylimino)-1,5-dideoxy-6-O-[1,1-dimethylethyl)diphenyl]-D-glucitol, (11.08 g, 242 mMol) and dibutyltinoxide (6.22 g) were suspended in methanol (150 mL), stirred magnetically, and heated to reflux. The reaction mixture became increasingly homogeneous with heating, and formed a clear solution after 1 hour at reflux. The methanol was removed by rotary evaporation. The product was twice diluted with toluene (20 mL) and re-concentrated. Final concentration (<0.5 torr ) afforded the title compound as a solid foam (16.68 g).

Anal. Calc. for $C_{34}H_{55}NO_4SiSn$: C, 59.30; H, 8.05; N, 2.03. Found: C, 59.03; H, 8.08; N, 1.95.

EXAMPLE 9

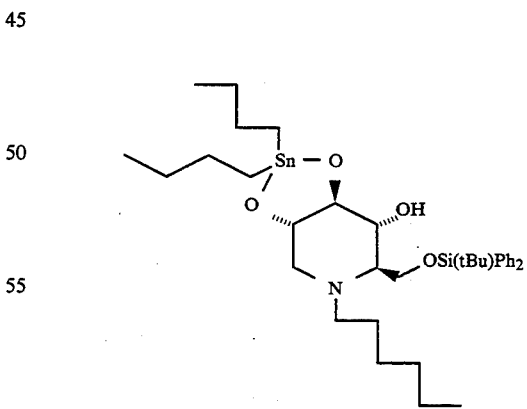

1,5-Dideoxy-2,3-O-(dibutylstannylene-6-O-[(1,1-dimethylethyl)diphenylsilyl]-1,5-(hexylimino)-D-glucitol The title compound was prepared by the method of Example 8 using the title compound of Example 2 in the place of the title compound of Example 1.

EXAMPLE 10

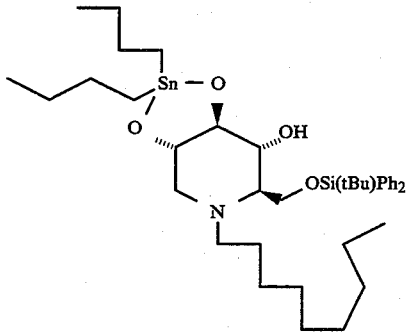

1,5-Dideoxy-2,3-O-(dibutylstannylene)-6-0-[(1,1-dimethylethyl)diphenylsilyl]-1,5-(nonylimino)-D-glucitol The title compound was prepared by the method of Example 8 using the title compound of Example 3 in the place of the title compound of Example 1.

EXAMPLE 11

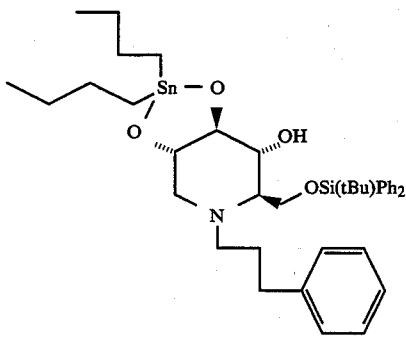

1,5-Dideoxy-2,3-O-(dibutylstannylene)-6-0-[(1,1-dimethylethyl) diphenylsilyl]-1,5-(3-phenyl)propylimino-D-glucitol The title compound was prepared by the method of Example 8 using the title compound of Example 4 in the place of the title compound of Example 1.

EXAMPLE 12

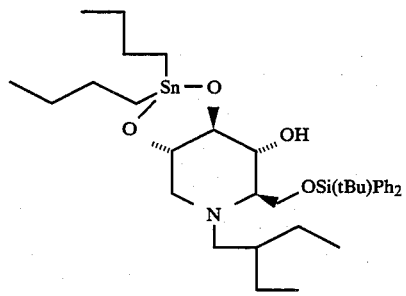

1,5-Dideoxy-2,3-O-(dibutylstannylene)-6-O-[(1,1-dimethylethyl) diphenylsilyl]-1,5- (2-ethylbutyl) imino-D-glucitol The title compound was prepared by the method of Example 8 using the title compound of Example 5 in the place of the title compound of Example 1.

EXAMPLE 13

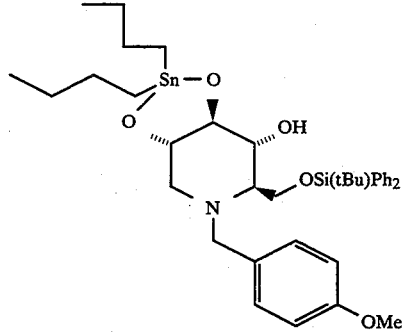

1,5-Dideoxy-2,3-0-(dibutylstannylene-6-0-[(1,1-dimethylethyl) diphenylsilyl]-1,5-[(4-methoxyphenyl)methyl]imino-D-glucitol The title compound was prepared by the method of Example 8 using the title compound of Example 6 in the place of the title compound of Example 1.

EXAMPLE 14

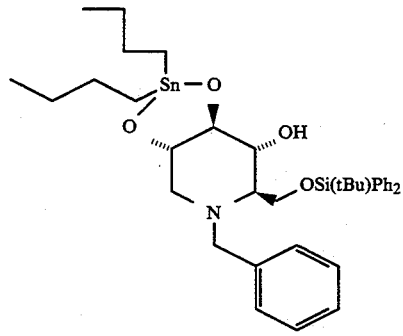

1,5-Dideoxy-2,3-O-(dibutylstannylene)-6-O-[(1,1-dimethylethyl)diphenylsilyl]-1,5-(phenylmethyl)imino-D-glucitol The title compound was prepared by the method of Example 8 using the title compound of Example 7 in the place of the title compound of Example 1.

EXAMPLE 15

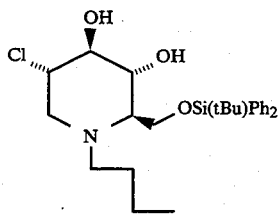

1,5-(Butylimino)-2-chloro-1,2,5-trideoxy-6-O-[(1,1-dimethylethyl) diphenylsilyl]-D-glucitol The title compound of Example 8, 1,5-(butylimino)-1,5-dideoxy-2,3-O-(dibutylstannylene)-6-O-[(1,1-dimethylethyl)diphenylsilyl]-D-glucitol, (6.03 g, 8.75 mMol) was diluted with dichloromethane (80 mL) and triethylamine (1.01 g). Toluenesulfonyl chloride (1.80 g) was added, and the reaction was stirred at ambient temperature for 4 hours. Concentration and chromatography afforded the title compound (3.59 g, 84%).

NMR (400 MHz, CDCl₃): 7.71–7.66 (m, 4H); 7.48–7.38 (m, 6H); 3.97 (dd, 1H, $J_1=11.0$ Hz, $J_2=3.5$ Hz); 3.85 (dd, 1H, $J_1=11.0$ Hz, $J_2=5.5$. Hz); 3.82 (ddd, 1H, $J_1=11.0$ Hz, $J_2=10.0$ Hz, $J_3=4.5$ Hz); 3.59 (dt, 1H, $J_1=9.5$ Hz, $J_2=2.0$ Hz); 3.50 (d, 1H, $J=2.0$ Hz); 3.43 (ddd, 1H, $J_1=10.0$ Hz, $J_2=9.5$ Hz, $J_3=1.0$ Hz); 3.10 (dd, 1H, $J_1,=11.5$ Hz, $J_2=4.5$ Hz); 2.57 (m, 1H); 2.50 (dd, 1H, $J_1=11.5$ Hz, $J_2=11.0$ Hz); 1.07 (5, 9H); 1.36–1.01 (m, 4H); 0.80 (t, 3H, $J=7.0$ Hz).

Anal. Calc. for $C_{26}H_{38}ClNO_3Si$: C, 65.59; H, 8.04; N, 2.94. Found: C, 65.66; H, 7.85; N, 2.87.

EXAMPLE 16

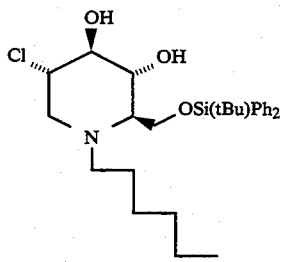

2-Chloro-1,2,5-trideoxy-6-O-[(1,1-dimethylethyl)diphenylsilyl]-1,5-hexylimino-D-glucitol The title compound was prepared by the method of Example 15 using the title compound of Example 9 (9.2 mM) in the place of the title compound of Example 8 and proceeding in 81% yield. The structure was confirmed by NMR.

EXAMPLE 17

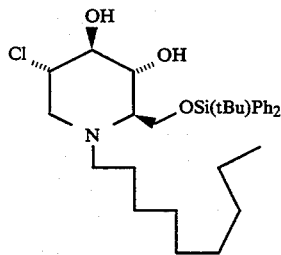

2-Chloro-1,2,5-trideoxy-6-O-[(1,1-dimethylethyl)diphenylsilyl]-1,5-nonylimino-D-glucitol The title compound was prepared by the method of Example 15 using the title compound of Example 10 (4.56 mM) in the place of the title compound of Example 8 and proceeding in 93% yield. The structure was confirmed by NMR.

EXAMPLE 18

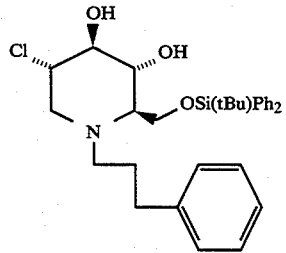

2-Chloro-1,2,5-trideoxy-6-O-[(1,1-dimethylethyl) -diphenylsilyl]-1,5- (3-phenyl)propylimino-D-glucitol.

The title compound was prepared by the method of Example 15, using the title compound of Example 11 (8.22 mM) in the place of the title compound of Example 8 and proceeding in 86% yield. The structure was confirmed by NMR.

EXAMPLE 19

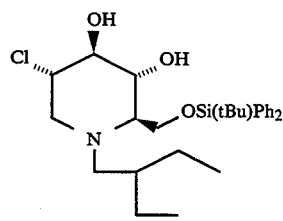

2-Chloro-1,2,5-trideoxy-6-O-[(1,1-dimethylethyl)-diphenylsilyl]-1,5- (2-ethylbutyl)imino-D-glucitol The title compound was prepared by the method of Example 15 using the title compound of Example 12 (1.19 mM) in the place of the title compound of Example 8 and proceeding in 81% yield. The structure was confirmed by NMR.

EXAMPLE 20

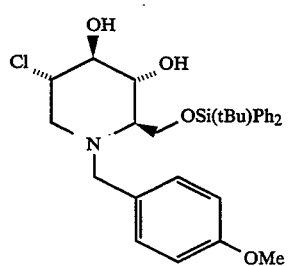

2-Chloro-1,2,5-trideoxy-6-O-[(1,1-dimethylethyl) diphenylsilyl) -diphenylsilyl]-1,5-[(4-methoxyphenyl)methyl]imino-D-glucitol The title compound was prepared by the method of Example using the title compound of Example 13 (2.951 g) in the place of the title compound of Example 8 and proceeding in 76% yield. The structure was confirmed by NMR.

EXAMPLE 21

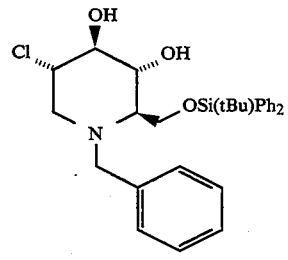

2-Chloro-1,2,5-trideoxy-[(1,1-dimethylethyl) -diphenylsilyl]-1,5-(phenylmethyl)imino-D-glucitol The title compound was prepared by the method of Example 15 using the title compound of Example 14 (4.0 mM) in the place of the title compound of Example 8 and proceeding in 83% yield. The structure was confirmed by NMR.

EXAMPLE 22

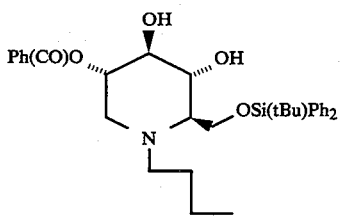

1,5-(Butylimino)-1,5-dideoxy-6-0-[(1,1-dimethylethyl)-diphenylsilyl]-D-glucitol, 2 -benzoate The title compound of Example 1, 1,5-(butylimino)-1,5-dideoxy-6-0-[1,1-dimethylethyl)diphenyl]-D-glucitol, (4.81 mmol, 2.20 g) was mixed with dibutyltin oxide (1.22 g) and diluted with methanol (50 mL). The reaction was brought to reflux for 1 hour, during which time the mixture became a homogeneous solution. The product was cooled, concentrated, and azeotroped with toluene (ca. 10 mL) to remove residual methanol. The resulting solid foam was diluted with dichloromethane (40 mL) and triethylamine (0.505 g) and benzoyl chloride (0.691 g) was added, maintaining the reaction mixture at ambient temperature. After stirring for 2 hours, the mixture was concentrated and subjected to silica gel chromatography. Concentration in vacuo afforded the title compound (1.811 g) in 67% yield as a solid form.

The structure was confirmed by $^1$H and $^{13}$C. NMR as well as microanalysis.

Anal. calc. for $C_{33}H_{43}NO_5Si$: C, 70.55; H, 7.71; N, 2.49. Found: C, 70.33; H, 7.86; N, 2.46.

EXAMPLE 23

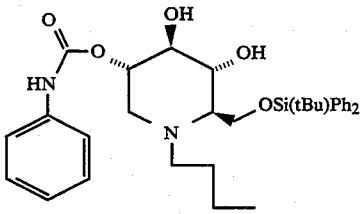

1,5-(Butylimino)-1,5-dideoxy-6-O-[(1,1-dimethylethyl)-diphenylsilyl]-D-glucitol, 2- (phenylcarbamoate)

The title compound of Example 8, 1,5-(butylimino)-1,5 -dideoxy-2,3-O-(dibutylstannylene)-6-O-[(1,1-dimethylethyl)diphenylsilyl]-D-glucitol, (1.106 g, 1.605 mM) was dissolved in dichloromethane (16 mL) and cooled to 0° C. Phenylisocyanate (0.190 g) was added, and the reaction was stirred at 0° C. for 2 hours. Concentration, followed by silica gel chromatography afforded the title compound (0.580 g, 65%). The structure was confirmed by $^1$H and $^{13}$C. NMR.

EXAMPLE 24

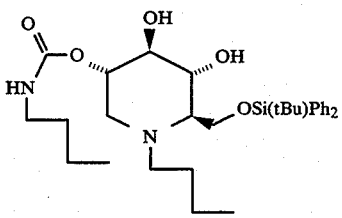

1,5-(Butylimino)-1,5-dideoxy-6-O-[(1,1-dimethylethyl) diphenylsilyl]-D-glucitol, 2-(butylcarbamoate)

The title compound was prepared by the method of Example 23 except that n-butylisocyanate was used in the place of phenylisocyanate and that the reaction was conducted at ambient temperature. From 1.80 g of the title compound of Example 8, 1.070 g (74%) of the title compound of this Example 24 was obtained. The structure was confirmed by NMR.

EXAMPLE 25

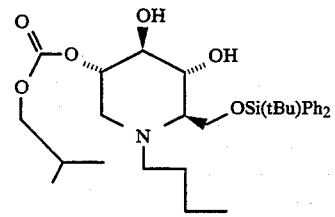

1,5-(Butylimino)-1,5-dideoxy-6-O-[(1,1-dimethylethyl) diphenylsilyl]-D-glucitol, 2- [(2 -methylpropyl)carbonate]

The title compound of Example 8, 1,5-butylimino)-1,5-dideoxy-2,3-O-(dibutylstannylene)-6-O-[1,1-dimethylethyl)-diphenylsilyl]-D-glucitol, (1.50 g, 2.18 mM) was dissolved in dichloromethane (22 mL) and triethylamine (0.253 g) was added. The mixture was cooled to 0° C., isobutylchloroformate (0.311 g) was added, and the reaction was stirred at room temperature for 2 hours. Thin layer chromatography indicated incomplete conversion. Additional isobutylchloroformate (0.17 g) was introduced and the reaction was continued an additional hour. Concentration, followed by silica gel chromatography afforded 1.089 g of the title compound (90%). The structure was confirmed by highfield $^1$H NMR.

EXAMPLE 26

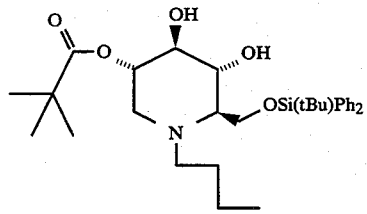

1,5 (Butylimino)-1,5-dideoxy-6-O-[(1,1-dimethylethyl) diphenylsilyl]-D-glucitol, 2- (2,2,2-trimethylacetate)

The title compound of Example 8 (0,594 g, 0.86 mM) was dissolved in dichloromethane (7.2 mL). Triethylamine (0.096 g) was added, followed by trimethylacetyl chloride (0,109 g). The reaction was stirred at room temperature for 4 days. On the fourth day, additional trimethylacetyl chloride (ca. 0.05 g) was added, and the reaction stirred an additional 4 hours. Concentration followed by chromatography afforded the title compound as an oil (0.369 g, 79%). MIR: 1726 $CM^{-1}$ (neat).

EXAMPLE 27

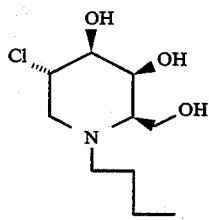

1,5-(Butylimino)-2-chloro-1,2,5-trideoxy-D-glucitol

The title compound of Example 15, 1,5-(butylimino)-2-chloro-1,2,5-trideoxy-6-O-[(1,1-dimethylethyl)diphenylsilyl]-D-glucitol, (0.121 g) was combined with KHF$_2$ (0.121 g) and methanol (2.5 mL) and stirred at ambient temperature for 5 hours, monitoring the course of reaction by thin-layer chromatography. Concentration, followed by silica gel chromatography afforded the title compound, which was further purified by recrystallization from methyl acetate/hexane (91%); mp=(DSC, 10° C./min) 112°–114° C.

NMR (400 MHz, CD$_3$OD): 3.86 (dd, 1H, J$_1$=12 Hz, J$_2$=2.5 Hz); 3.83 (dd, 1H, J$_1$=12 Hz, J$_2$=2.5 Hz); 3.73 (ddd, 1H, J$_1$=11.0 Hz, J$_2$=10.0 Hz, J$_3$=4.5 Hz); 3.37 (dd, 1H, J$_1$=10.0 Hz; J$_2$=9.0 Hz); 3.23 (dd, 1H, J,=10.0 Hz, J$_2$=9.0 Hz); 3.15 (dd, 1H, J=11.5 Hz, J$_2$=4.5 Hz); 2.80 (m, 1H); 2.62 (m, 1H ); 2.46 (dd, 1H, J$_1$=11.5 Hz, J$_2$=11.0 Hz); 2.18 (dt, 1H, J,=9.5 Hz, J$_2$=2.5 Hz); 1.46 (m, 2H); 1.37–1.29 (m, 2H); 0.95 (t, J=7.0 Hz)

Anal. calc. for C$_{10}$H$_{20}$ClNO$_3$: C, 50.74; H, 8.09; N, 5.92. Found: C, 50.37; H, 8.39; N, 5.76.

EXAMPLE 28

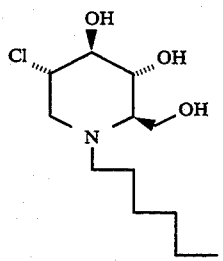

2-Chloro-1,2,5-trideoxy-1,5(hexylimino)-D-glucitol

The title compound was prepared by the method of Example 27, using the title compound of Example 16 in the place of the title compound of Example 15. Recrystallization was from methyl acetate/hexane (80%); mp=(DSC, 10° C./min) 102°–104° C.

Anal. calc. for C$_{12}$H$_{24}$ClNO$_3$: C, 54.23; H, 9.10; N, 5.27. Found: C, 54.56; H, 9.27; N, 5.03.

EXAMPLE 29

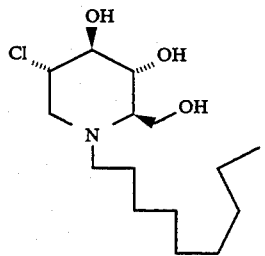

2-Chloro-1,2,5-trideoxy-1,5-(nonylimino)-D-glucitol

The title compound was prepared by the method of Example 27 using the title compound of Example 17 in the place of the title compound of Example 15. Recrystallization was from methyl acetate/hexane (41%); mp=(DSC, 10° C./min) 110°–111° C.

Anal. calc. for C$_{15}$H$_{30}$ClNO$_3$: C, 58.52; H, 9.82; N, 4.52. Found: C, 58.59; H, 10.00; N, 4.43.

EXAMPLE 30

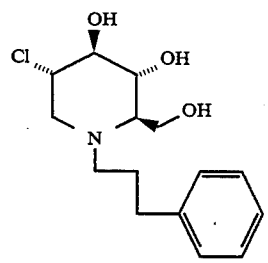

2-Chloro-1,2,5-trideoxy-1,5- (3-phenyl) propylimino-D-glucitol

The title compound was prepared by the method of Example 27 using the title compound of Example 18 in the place of the title compound of Example 15. Recrystallization was from methyl acetate/hexane (68%). The structure was confirmed by NMR.

EXAMPLE 31

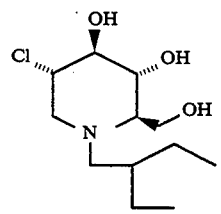

2-Chloro-1,2,5-trideoxy-(2-ethyl)butylimino-D-glucitol

The title compound was prepared by the method of Example 27 using the title compound of Example 19 in the place of the title compound of Example 15. Recrystallization was from methyl acetate/hexane (39%). The structure was confirmed by NMR.

EXAMPLE 32

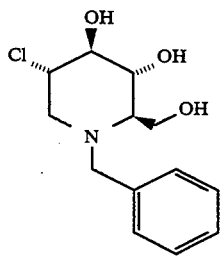

2-Chloro-1,2,5-trideoxy-1,5- (phenylmethyl) imino-D-glucitol

The title compound was prepared by the method of Example 27 using the title compound of Example 21 in the place of the title compound of Example 15. Recrystallization was from methyl acetate/hexane (19%); mp=(DSC, 10° C./min) 138°–140° C.

Anal. calc. for $C_{13}H_{18}ClNO_3$: C, 57.46; H, 6.68; N, 5.15. Found: C, 57.12; H, 6.58; N, 4.97.

EXAMPLE 33

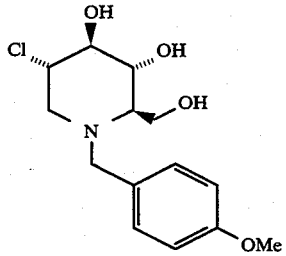

2-Chloro-1,2,5-trideoxy-1,5-[(4-methoxyphenyl)methylimino]-D-glucitol

The title compound of Example 20, 2-chloro-1,2,5-trideoxy-6-O-[(dimethylethyl)diphenylsilyl]-1,5-[(4-methoxyphenyl)methyl]imino-D-glucitol, (1.609 g, 2.99 mM) was diluted with methanol (50 mL), and potassium hydrogen flouride (1.6 g) was added. After 4 hours of stirring, the reaction mixture was stored unstirred at 5° C.±2° C. for 40 hours, concentrated, and purified by silica gel chromatography (95:5 ethyl acetate: methanol). Recrystallization from methyl acetate/-hexane afforded 0.631 g (70%) of the title compound, which was recrystallized a second time and characterized: mass spectrum, m/e 302 (MH+). mp=(DSC, 10° C./min) 150°-152° C.

($^1$H NMR, CD$_3$OD): 7.24 (m, 2H); 6.88 (m, 2H); 4.14 (d, 1H, J=13.5 Hz); 4.08 (dd, 1H, J$_1$=12.0 Hz, J$_2$=2.5 Hz); 3.93 (dd, 1H, J$_1$=12.0 Hz); 3.78 (S, 3H); 3.64 (ddd, 1H, J$_1$=11.0 Hz, J$_2$=10.0 Hz, J$_2$=4.4 Hz); 3.42 (dd, 1H, J$_1$=9.5 Hz, J$_2$=9.0 Hz); 3.27 (d, 1H, J=13.5 Hz); 3.22 (dd, J$_1$=10.0 Hz, J$_2$=9.0 Hz); 2.98 (dd, 1H, J$_1$=12.0 Hz, J$_2$=4.5 Hz); 2.19 (ddd, 1H, J$_1$=9.5 Hz, J$_2$=3.0 Hz, J$_3$=2.5 Hz); 2.15 (dd, 1H, J$_1$=12.0 HZ, J$_2$=11.0 Hz).

Anal. calc. for $C_{14}H_{20}ClNO_4$: C, 55.72; H, 6.68; N, 4.64. Found: C, 55.73; H, 6.70; N, 4.64.

EXAMPLE 34

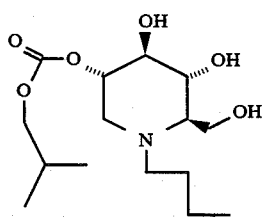

1,5(Butylimino)-1,5-dideoxy-D-glucitol, 2-[(2-methylpropyl)-carbonate]

The title compound was prepared by the method of Example 27 using the title compound of Example 25 in the place of the title compound of Example 15. Recrystallization was from ethyl acetate (76%); mp=(DSC, 10° C./min) 99°-102° C. $^{13}$C. NMR (100 MHz, CD$_3$OD): 156.3, 77.4, 76.5, 74.9, 71.7, 67.0, 59.2, 54.0, 53.1, 28.9, 27.3, 21.5, 19.0, 14.2

EXAMPLE 35

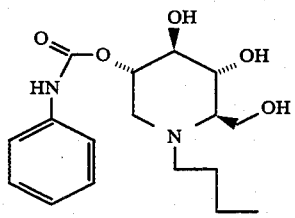

1,5-(Butylimino)-1,5-dideoxy-D-glucitol, 2-phenylcarbamoate)

The title compound was prepared by the method of Example 27 using the title compound of Example 23 in the place of the title compound of Example 15. Recrystallization was from methyl acetate/hexane (65%); mp=(DSC, 10° C./min) 168°-169° C.

Anal. calc. for $C_{17}H_{26}N_2O_5$: C, 60.33; H, 7.75; N, 8.28. Found: C, 60.06; H, 7.73; N, 8.09.

EXAMPLE 36

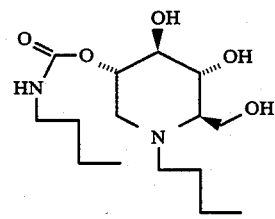

1,5- (Butylimino) -1,5-dideoxy) -D-glucitol, 2- (butylcarbamoate)

The title compound was prepared by the method of Example 27 using the title compound of Example 24 in the place of the title compound of Example 15. Recrystallization was from methyl acetate/hexane. mp=(DSC, 10° C./min) 175°-176° C.

Anal. calc. for $C_{15}H_{30}N_2O_5$: C, 56.58; H, 9.50; N, 8.80. Found: C, 56.54; H, 9.57; N, 8.72.

EXAMPLE 37

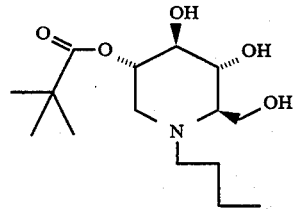

1,5-(Butylimino)-1,5-dideoxy-D-glucitol, 2-trimethylacetate

The title compound of Example 26, 1,5(butylimino)-1,5-dideoxy-6-O-[(1,1-dimethylethyl)diphenylsilyl]-D-glucitol, 2-(2,2,2-trimethylacetate), (0.352 g) was diluted with methanol (5 mL). KHF$_2$ (350 mg) was added, and the mixture was stirred for 4 hours at ambient temperature. Concentration followed by chromatography afforded the title compound (0.190 g) as a viscous oil (96%). The structure was confirmed by NMR.

Anal. calc. for $C_{15}H_{29}NO_5$: C, 59.38; H, 9.63; N, 4.62. Found: C, 58.94; H, 9.88; N, 4.48.

EXAMPLE 38

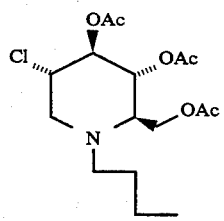

1,5-(Butylimino)-2-chloro-1,2,5-trideoxy-D-glucitol, triacetate

The title compound of Example 27, 1,5-(butylimino)-2-chloro-1,2,5-trideoxy-D-glucitol, (0.166g, 0.70 mM) was suspended in dichloromethane (5 mL). Triethylamine (0.47 g) was added, followed by acetic anhydride (0.44 g). The reaction was stirred overnight, diluted with ethyl acetate (40 mL) and washed with saturated NaHCO3 solution (10 mL). The organic layer was dried using MgSO4, concentrated and the residue subjected to silica gel chromatography. The material was further purified by recrystallization from ether/hexane, affording the title compound (0.163 mg, 66%): m.p. (DSC, 10° C./min) 62°–65°.

NMR (400 MHz, CDCl3): 5.05–4.98 (m, 2H); 4.17 (dd, 1H, $J_1=12.0$ Hz, $J_2=3.0$ Hz); 4.14 (dd, 1H, $J_1=12.0$ Hz, $J_2=2.5$ Hz); 3.94 (m, 1H); 3.26 (dd, 1H, $J_1=120$ Hz, $J_2=5.0$ Hz); 2.78–2.67 (m, 2H); 2.60 (m, 1H); 2.59 (dd, 1H, $J_1=12.0$, $J_2=11.5$); 2.08 (S, 6H); 2.02 (S, 3H); 1.50–1.22 (m, 4H); 0.92 (t, 3H, J=7.5 Hz)

Anal. calc. for $C_{16}H_{26}ClNO_6$: C, 52.82; H, 7.20; N, 3.85. Found: C, 53.13; H, 7.36; N, 3.81.

EXAMPLE 39

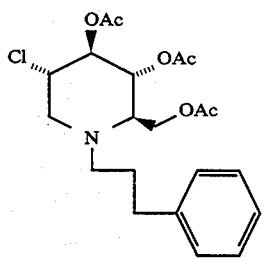

2-Chloro-1,2,5-trideoxy-1,5-(3-phenyl)propylimino -D-glucitol, triacetate

The title compound was prepared by a method analogous to the method of Example 38 except the title compound of Example 30 (0.100 g) was used in the place of the title compound of Example 27 and a non-aqueous workup was used. After complete reaction (2 hours), methanol (ca. 1 mL) was added, and, after an additional 10 min, the mixture was concentrated and subjected to silica gel chromatography, affording the title compound (0.118 g) as an oil. The structure was verified by NMR.

Anal. calc. for $C_{21}H_{28}ClNO_6$: C, 59.21; H, 6.63; N, 3.29. Found: C, 59.26; H, 6.39; N, 3.28.

EXAMPLE 40

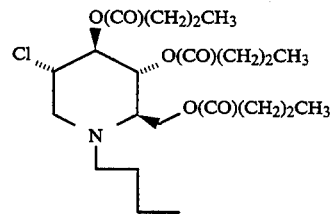

1,5-(Butylimino)-2-chloro-1,2,5-trideoxy-D-glucitrol, tributyrate

The title compound was prepared by the method of Example 39 using butyric anhydride in the place of acetic anhydride. From 0.160 g of 1,5-(butylimino)-2-chloro -1,2,5-trideoxy-D-glucitol, 0.307 g (98%) of the title compound was obtained as an oil.

Anal. calc. for $C_{22}H_{38}ClNO_6$: C, 58.98; H, 8.55; N, 3.13. Found: C, 58.92; H, 8.57; N, 3.08.

EXAMPLE 41

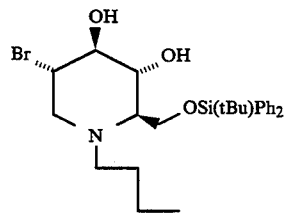

2-Bromo-1,5-(butylimino)-1,2,5-trideoxy-6-0- [(1,1-dimethylethyl) diphenylsilyl]-D-glucitol The title compound of Example 8 (0.953 g, 1.38) was dissolved in dichloromethane (11 mL). Triethylamine (0.162 g) was added, followed by N,N-dimethylaminopyridine (8 mg) and toluenesulfonyl bromide (0.32 g). After stirring the reaction mixture at ambient temerature for 5 hours, solvent was removed by rotary evaporation, and the crude product was purified by silica gel chromatography, affording the title compound as an oil (0.55 g, 89%). The structure was confirmed by high-field $^1H$ and $^{13}C$ NMR. Mass spectrum m/e 520, 522 (MH+).

EXAMPLE 42

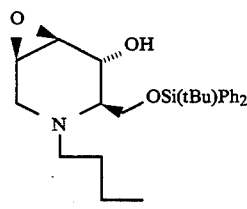

2,3-Anhydro-1,5-(butylimino)-1,5-dideoxy-6-0-[(1,1-dimethylethyl) diphenylsilyl]-D-mannitol To a solution of the title compound of Example 41 (0.723 g, 1.39 mM) in dichloromethane (14 mL) was added 1,8-diazabicylclo [5.4.0]undec-7-ene (DBU) (0.211 g). The mixture was stirred at ambient temperature for 24 hours, at which point additional DBU (ca. 0.05 mL) was added and stirring continued for 6 more hours. Concentration and chromatography afforded the title compound (0.332 mg, 75%) as an oil. The structure was confirmed by high-field NMR.

EXAMPLE 43

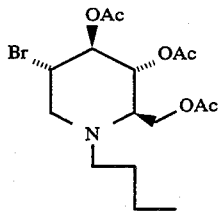

2-Bromo-1,5-butylimino-1,2,5-trideoxy-D-glucitol, triacetate

The title compound of Example 41 (900 mg, 1.73 mmol) was diluted with dichloromethane (20 mL). Pyridine (174 g) was added, followed by acetic anhydride (1.84 g). The reaction was maintained at ambient temperature during the addition, and stirred for 1.5 hours. Additional pyridine (0.49 g) and acetic anhydride (0.54 g) were added. After 15 minutes, 30% hydrogen fluoride-pyridine (1 mL) was added, dropwise, using a polyethylene syringe fitted with a stainless steel needle. The mixture was stirred overnight, acetic hydride (0.11 g) was added, and the mixture was stirred one additional hour. The mixture was diluted with ethyl acetate (80 mL) and washed with half-saturated $NaHCO_3$ solution (10 mL). The organic layer was dried using magnesium sulfate, concentrated, and the residue subjected to silica gel chromatography, affording, on concentration, the title compound (0,249 g, 35% as an oil. Mass spectrum, m/e 408, 410 (MH+)

Anal. calc. for ($C_{16}H_{26}NO_6Br$): C, 47.06; H, 6.41; N, 3.43. Found: C, 47.25; H, 6.41; N, 3.50.

EXAMPLE 44

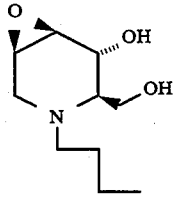

2,3-Anhydro-1,5-(butylimino)-1,5-dideoxy-D-mannitol

The title compound of Example 42 (1,016 g) was dissolved in methanol (24 mL) and $KHF_2$ (1.0 g) was added. The mixture was stirred at ambient temperature for 2 hours, concentrated and subjected to chromatography to afford the title compound as an oil (366 mg). The structure was confirmed by NMR. $^{13}C$ NMR (100 MHz, $CDCl_3$): 66.0, 63.9, 59.9, 53.6, 52.9, 51.5, 47.4, 28.9, 20.3, 13.9.

EXAMPLE 45

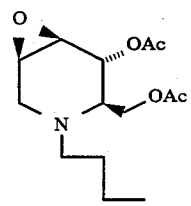

2,3-Anhydro-1,5-(butylimino)-1,5-dideoxy-D-mannitol, diacetate

The title compound of Example 44 (0.187 g, 1 mM) was diluted with dichloromethane (3 mL). Triethylamine (0.505 g) and N,N-dimethylaminopyridine (1.5 mg) were added, followed by acetic anhydride (0.459 g). After 1 hour, the mixture was concentrated and purified by silica gel chromatography to afford the title compound (0.198 g, 67%) as an oil.

mass spectrum (m/e) 286 (MH+)

$^{13}C$ NMR (100 MHz, $CDCl_3$): 171.0, 170.2, 66.8, 60.0, 57.8, 53.1, 51.5, 51.3, 472, 28.9, 21.1, 21.0, 20.4, 14.0

Anal. calc. for $C_{14}H_{23}NO_5 = \frac{1}{3} H_2O$: C, 57.71; H, 8.19: N, 4.81. Found: C, 57.85; H, 8.03; N, 4.72.

EXAMPLE 46

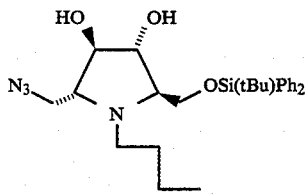

(A) 1-Azido-2,5-(butylimino)-1,2,5-trideoxy-6-0-[(1,1-dimethylethyl)diphenylsilyl)-D-mannitol

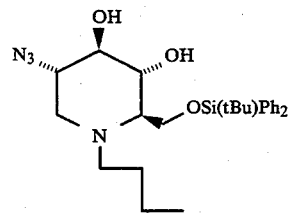

(B) 2-Azido-1,5-(butylimino)-1,2,5-trideoxy-6-0-[(1,1-dimethlethyl)diphenylsilyl)-D-glucitol The title compound of Example 15 (52 mg) was combined with sodium azide (14 mg) and acetonitrile (1 mL). The mixture was heated to 60° C. for 5.5 hours and allowed to stand at ambient temperature overnight- Concentration followed by chromatography afforded the title compounds (B) (22 rag) and (A) (16 mg) as oils.

46(B)

400 MHz NMR ($CDCl_3$):

7.70–7.66 (m, 8H); 7.49–7.38 (m, 12H); 3.96 (dd, 1H, $J_1=10.5$ Hz, $J_2=3.5$ Hz); 3.82 (dd, 1H, $J_1=10.5$ Hz, $J_2=6.0$ Hz); 3.68 (br.s 1H); 3.57 (t, 1H, J=8.5 Hz); 3.46 (ddd, 1H, $J_1=11.0$, $J_2=9.5$ Hz, $J_3=4.5$ Hz); 3.36 (dd, 1H, $J_1=9.5$ Hz, $J_2=8.5$ Hz); 2.93 (dd, 1H, $J_1=11.5$ Hz, $J_2=4.5$ Hz); 2.89 (br.s, 1H); 2.51 (m, 1H); 2.37–2.30 (m, 2H); 2.22 (dd, 1H, $J_1=11.5$, $J_2=11.0$ Hz); 1.07 (s, 9H); 1.34–0.99 (m, 4H); 0.78 (t, 3H, J=7.5 Hz)

46(A)

$^{13}$C. NMR(100 MHz, CDCl$_3$, partial): 80.3, 79.7, 69.2, 69.0, 62.3, 50.8, 46.5, 30.5, 26.8, 20.5, 18.9, 14.0

EXAMPLE 47

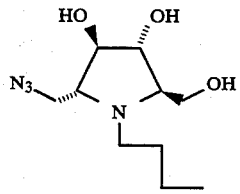

1-Azido-2,5-(butylimino)-1-2,5-trideoxy-D-mannitol

The title compound of Example 46(A), (302 mg) was diluted with methanol (6 mL) and KHF$_2$ (302 mg) was added. The mixture was stirred 5 hours at ambient temperature, concentrated and subjected to chromatography. The title compound was obtained as an oil.

NMR (400 MHz, CD$_3$OD): 3.94 (t, 1H, J=3Hz); 3.85 (dd, 1H, J$_1$=3.5 Hz, J$_2$=3.0 Hz); 3.74 (dd, 1H, J$_1$=11.5 Hz, J$_2$=3.0 Hz); 3.65 (dd, 1H, J$_1$=11.5 Hz, J$_2$=3.5 Hz); 3.49 (dd, 1H, J$_1$=12.5 Hz, J$_2$=6.5); 3.46 (dd, 1H, J$_1$=12.5, J$_2$=4.5 Hz); 3.04 (ddd, 1H, J$_1$=6.5 Hz, J$_2$=4.5 Hz, J$_3$=3.5 Hz); 2.97 (dt, 1H, J$_1$=5.0 Hz, J$_2$=3.5 Hz); 2.66-2.77 (m, 2H); 1.28-1.58 (m, 4H); 0.94 (t, 3H, J=7.5 Hz).

EXAMPLE 48

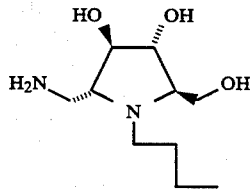

1-Amino-2,5-butylimino)-1,2,5-trideoxy-D-mannitol

The title compound of Example 47 (0.491 mg) was diluted with methanol and hydrogenated at ambient temperature and pressure over 4% Pd/C in a Parr shaker for 9 hours. Filtration and concentration afforded the title compound as a solid (quant.).

$^{13}$C. NMR (125 MHz, CD$_3$OD): 81.3, 80.8, 71.7, 70.3, 60.8, 40.8, 31.9, 21.7, 14.4.

Anal. calc. for C$_{10}$H$_{22}$N$_2$O$_3$: C, 55.02; H, 10.16; N, 12.83. Found: C, 54.79; H, 10.27; N, 12.46.

EXAMPLE 49

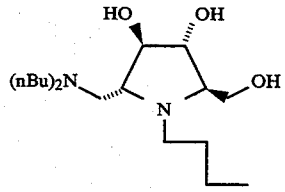

2,5-(Butylimino)-1-(dibutylamino)-1,2,5-trideoxy-D-mannitol

The title compound of Example 47 (170 mg) was diluted with methanol and hydrogenated at ambient pressure and temperature in the presence of n-butyraldehyde in a Parr shaker for 50 hours. Filtration, followed by concentration and chromatography afforded the title compound as an oil (quant.). The structure was confirmed by NMR.

EXAMPLE 50

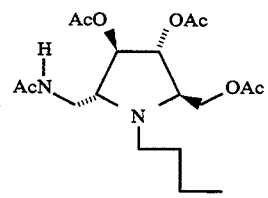

1-(Acetylamino)-2,5-(butylimino)-1,2,5-trideoxy-D-mannitol, 3,4,6-triacetate

The title compound of Example 48 (0.277 g) was combined with dichloromethane (8 mL), triethylamine (1.18 mL), and N,N-dimethylaminopyridine. Acetic anhydride (0.77 mL) was added, and the mixture was stirred under argon at ambient temperature for 20 hours. The mixture was diluted with saturated NaHCO$_3$ solution and extracted with ethyl acetate (2×50 mL). The combined organic phases were dried over magnesium sulfate, concentrated, and subjected to silica gel chromatography, affording, on concentration, the title compound (470 mg) as an oil.

$^{13}$C. NMR (100 MHz, CDCl$_3$): 170.7, 170.6, 170.4, 169.9, 79.9, 78.5, 65.6, 63.5, 60.9, 46.0, 37.8, 29.9, 23.2, 21.0, 20.9, 20.4, 13.9.

EXAMPLE 51

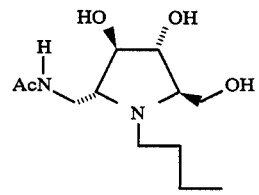

1-(Acetylamino)-2,5-(butylimino)-1,2,5-trideoxy-D-mannitol

The title compound of Example 50 (177 mg) was diluted with methanol (2.4 mL), water (0.3 mL), and triethylamine (0.3 mL), then stirred for 20 hours. The solution was azeotroped with toluene (3 mL), and subjected to chromatography, affording the title compound (108 mg) as an oil.

$^{13}$C. NMR (100 MHz, CD$_3$OD): 173.4, 81.2, 80.9, 70.2, 69.2, 60.6, 47.6, 39.4, 31.5, 22.6, 21.5, 14.3.

EXAMPLE 52

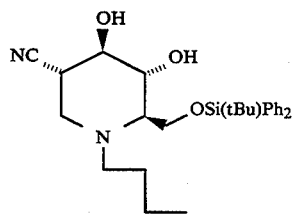

(A) 1,5-(Butylimino)-2-cyano-1,2,5, -trideoxy-6-O-[(1,1-dimethylethyl) diphenylsilyl]-D-glucitol

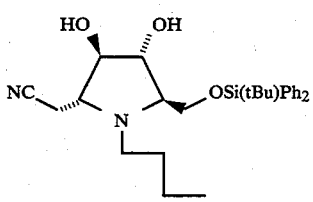

(B) 3,6-(Butylimino)-2-cyano-1,2,5-trideoxy-7-O-[(1,1-dimethylethyl)diphenylsilyl]-D-manno-heptanonitrile The title compound of Example 15 (2.604 g) was diluted with acetonitrile (55 mL). Sodium cyanide was added, and the mixture was stirred at reflux for 4.25 hours.

The mixture was concentrated, then filtered through silica gel, eluting with ethyl acetate. The solution was re-concentated and subjected to silica gel chromatography affording two oils: the title compounds (B) (310 mg) and (A) (580 mg).
52(A)
$^{13}$C NMR (125 MHz, CDCl$_3$): 135.6, 135.5, 132.4, 132.4, 130.2, 130.1, 128.3, 128.0, 127 9, 118.7, 74.8, 74.4, 64.2, 63.2, 52.1, 51.9, 33.8, 26.9, 26.8, 20.3, 19.1, 13.8.
52(B)
$^{13}$C NMR (125 MHz, CDCl$_3$) (partial): 118.7, 79.9, 79.5, 69.6, 64.5, 46.3, 30.9, 26.8, 20.6, 16.5, 14.0

EXAMPLE 53

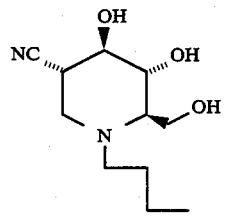

1,5-Butylimino-2-cyano-1,2,5-trideoxy-D-glucitol

The title compound of Example 52 (A) was diluted with methanol (8 mL), combined with KHF$_2$ (300 mg) and allowed to stir at room temperature for 5 hours. Concentration followed by chromatography afforded the title compound (105 mg) as a solid.

Anal. calc. for C$_{11}$H$_{20}$N$_2$O$_3$: C, 57.87; H, 8.83; N, 12.27. Found: C, 57.40; H, 8.89; N, 11.83.

EXAMPLE 54

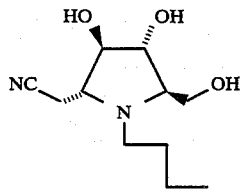

3,6-(Butylimino)-2,3,6-trideoxy-D-manno-heptanonitrile

To the title compound of Example 52(B) (560 mg) was added KHF$_2$ (560 mg) and methanol. The mixture was stirred 24 hours at room temperature, concentrated, and subjected to chromatography, affording the title compound (205 mg) as a solid.

Anal. calc. for C$_{11}$H$_{20}$N$_2$O$_3$: C, 57.87; H, 8.83; N, 12.27. Found: C, 57.77; H, 8.90; N, 12.09.

EXAMPLE 55

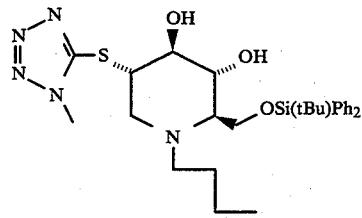

(A) 1,5-(Butylimino)-1,5-dideoxy-6-O-[(1,1-dimethylethyl) diphenylsilyl]-2-S-(1-methyl-1H-tetrazol-5-yl)-2-thio-D-glucitol

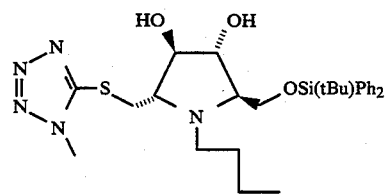

(B) 2,5-(Butylimino)-2,5-dideoxy-6-O-[(1,1-dimethylethyl) diphenylsilyl]-1S-(1-methyl-1H-tetrazol-5-yl)-1-thio-D-mannitol The title compound of Example 15 (1.929 g) was combined with 5-mercapto-l-methyltetrazole, sodium salt hydrate (0.783 g) and acetonitrile (20 mL). The mixture was stirred at reflux for 3 hours, concentrated, and filtered through a plug of silica gel, eluting with ethyl acetate. Concentration afforded 2.33 g of an oil containing a mixture of the title compounds (A) and (B). The isomers were not separable; the product was carried crude through the next synthetic transformation in Example 56.

EXAMPLE 56

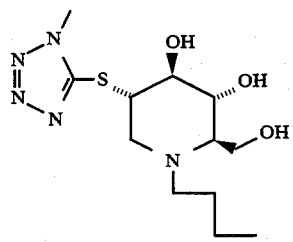

(A) 1,5-(Butylimino)-1,5-dideoxy-2-S-(1-methyl-1H-tetrazol-5-yl)-2-thio-D-glucitol

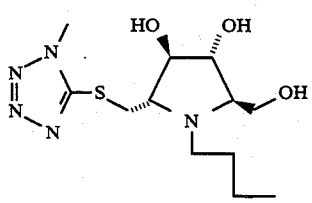

(B) 2,5-(Butylimino)-2,5-dideoxy-1S-(1-methyl-1H-tetrazol-5-yl)-1-thio-D-mannitol To 2.13 g of a crude mixture of the title compounds (A) and (B) of Example 55 was added KHF$_2$ (2.13 g) followed by methanol (50 mL). The reaction was stirred at ambient temperature for 4.5 hours, concentrated, and subjected to silica gel chromatography affording, in several operations, the title compound (A), a solid (240 mg); the title compound (B), an oil (381 mg); and a mixed fraction (90 mg).

56(A)

$^{13}$C NMR (125 MHz, CD$_3$OD) (Partial): 77.2, 73.6, 67.3, 59.6, 57.0, 52.9, 50.9, 34.3, 28.0, 21.6, 14.3.

56(B)

$^{13}$C NMR (125 MHz, CD$_3$OD) (Partial): 81.2, 80.8, 70.2, 68.4, 60.9, 47.4, 34.0, 33.9, 31.5, 21.6, 14.4.

EXAMPLE 57

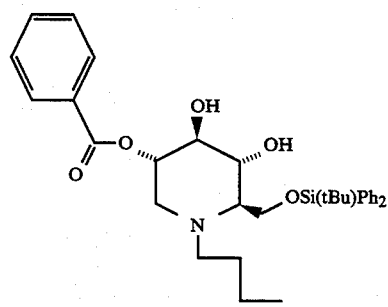

(A)  1,5-(Butylimino)-1,5-dideoxy-6-O-[(1,1-dimethylethyl) diphenylsilyl]-D-glucitol, 2-benzoate

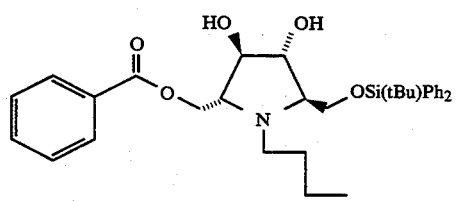

(s) 2,5-(Butylimino)-2,5-dideoxy-6-O-[(1,1-dimethyl)-diphenyl]silyl-D-mannitol, 1-benzoate The title compound of Example 15, (1.538 g) was combined with sodium benzoate (0.930 g) and acetonitrile (15 mL). The mixture was stirred at reflux for 3 hours, concentrated, and filtered through a silica plug, eluting with ethyl acetate. The crude product was subjected to chromatography, affording the title compound (A) as a white foam (1.465 g) and the title compound (B) as an oil (287 mg).

57(A)

Anal. calc. for C$_{18}$H$_{43}$NO$_5$Si: C, 70.55; H, 7.71; N, 2.49. Found: C, 70.33; H, 7.86, N, 2.46.

EXAMPLE 58

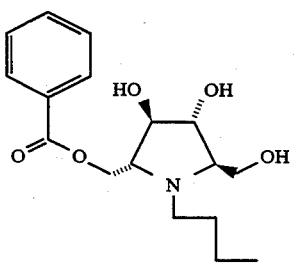

2,5-(Butylimino)-2,5-dideoxy-D-mannitol, 1-benzoate

The title compound of Example 57(B) (269 mg) was diluted with methanol (8 mL) and stirred in the presence of KHF$_2$ (269 mg) for 4 hours. Concentration followed by silica gel chromatography afforded the title compound as a hygroscopic oil (122 mg). The structure was confirmed by NMR.

EXAMPLE 59

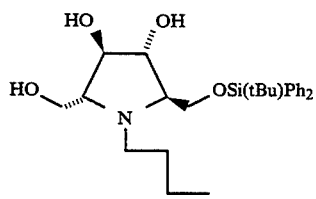

2,5-(Butylimino)-2,5-dideoxy-6-O-[(1,1-dimethylethyl) diphenyl]silyl-D-mannitol

To a solution of the title compound of Example 57(B) (320 mg) in methanol (5.7 mL) was added sodium methoxide (3 mg). After 4 hours of stirring, additional sodium methoxide (3 mg) was added and stirring was maintained another 20 hours. Concentration followed by chromatography afforded the title compound (188 mg) as an oil. The structure was confirmed by NMR.

Anal calc for C$_{26}$H$_{39}$NO$_4$Si.½ H$_2$O: C, 66.91; H, 8.64; N, 3.00. Found: C, 66.77; H, 8.62; N, 2.90.

EXAMPLE 60

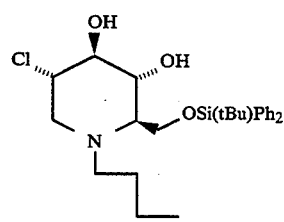

1,5-(Butylimino)-2-chloro-1,2,5-trideoxy-6-O-[(1,1-dimethylethyl) diphenylsilyl]-D-glucitol To a solution of the title compound of Example 59 (18 mg) in dichloromethane (0.5 mL) was added triethylamine (0.007 mL), 4-dimethylaminopyridine (0.1 mg), and toluenesulfonyl chloride (8.0 mg). The mixture was stirred at ambient temperature for 5 hours, additional toluenesulfonyl chloride (0.5 mg) was added, and stirring was continued another 16 hours. Concentration followed by chromatography afforded the title compound (8.1 mg). The NMR was identical to that of Example 15.

EXAMPLE 61

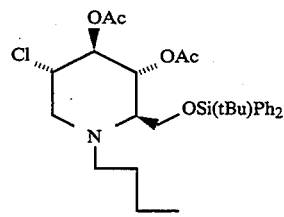

1,5-(Butylimino)-2-chloro-1,2,5-trideoxy-6-O-[(1,1-dimethylethyl) diphenylsilyl]-D-glucitol, diacetate The title compound of Example 15 (76 mg, 0.16 mM) was diluted with dichloromethane (1 mL). Triethylamine (0.07 mL, 0.5 mM) and 4-dimethylaminopyridine (0.1 mg) were added, followed by acetic anhydride (0.046 mL, 0.48 mM). After stirring the solution for 4 hours at ambient temperature, the solvent was removed by rotary evaporation and the residue was purified by silica gel chromatography to afford the title compound as a solid (82 mg). Mass spectrum m/e 560 (M+).

NMR (400 MHz, CDCl$_3$): 7.63 (m, 2H); 7.59 (m, 2H); 7.42 (m, 2H); 7.37 (m, 4H); 4.97 (m, 1H); 4.93 (m, 1H); 3.92 (m, 1H); 3.68 (dd, 1H, J$_1$=12 Hz, J$_2$=4.0 Hz); 3.65 (dd, 1H, J$_1$=12 Hz, J$_2$=2.0 Hz); 3.25 (dd, 1H, J$_1$=12 Hz, J$_2$=4.5 Hz); 2.88 (m, 1H); 2.59–2.51 (m, 2H); 2.50 (dd, 1H, J$_1$=12 Hz, J$_2$=11 Hz); 2.05 (s, 3H); 1.75 (s, 3H); 1.40 (m, 2H); 1.18 (m, 2H); 1.06 (s, 9H); 0.87 (t, 3H, J=7.5 Hz).

Anal. calc. for C$_{30}$H$_{42}$NO$_5$ClSi ($\frac{1}{2}$× H$_2$O): C, 63.81; H, 7.59; N, 2.48. Found: C, 63.61; H, 7.78; N, 2.43.

EXAMPLE 62

Various illustrative compounds synthesized above were tested for inhibition of visna virus in vitro in a plaque reduction assay (Method A) or for inhibition of HIV-1 in a test which measured reduction of cytopathogenic effect in virus-infected syncytium-sensitive Leu-3a-positive CEM cells grown in tissue culture (Method B) as follows:

Method A

Cell and virus propagation

Sheep choroid plexus (SCP) cells were obtained from American Type Culture Collection (ATCC) catalogue number CRL 1700 and were routinely passaged in vitro in Dulbecco's Modified Eagles (DME) medium supplemented with 20% fetal bovine serum (FBS). SCP cells were passaged once per week at a 1:2 or 1:3 split ratio. Visna was titrated by plaque assay in six-well plates. Virus pools were stored at −70° C.

Plaque reduction assay

SCP cells were cultured in 6-well plates to confluence. Wells were washed two times with serum free Minimal Essential Medium (MEM) to remove FBS. 0.2 ml of virus was added per well in MEM supplemented with 4 mM glutamine and gentamycin. After 1 hour adsorption, the virus was aspirated from each well. The appropriate concentration of each compound in 5 ml of Medium 199 (M-199) supplemented with 2% lamb serum, 4 mM glutamine, 0.5% agarose and gentamycin was added to each well. Cultures were incubated at 37° C. in a humidified 5% CO$_2$ incubator for 3–4 weeks. To terminate the test, cultures were fixed in 10% formalin, the agar removed, the monolayers stained with 1% crystal violet and plaques counted. Each compound concentration was run in triplicate. Control wells (without virus) were observed for toxicity of compounds at the termination of each test and graded morphologically from 0 to 4. 0 is no toxicity observed while 4 is total lysing of the cell monolayer.

96 well plate assay

The 96 well plate assay was performed similarly to the plaque assay above with modifications. SCP cells were seeded at 1×10$^4$ cells per well in 0.1 ml DME medium. When confluent, the wells were washed with serum free MEM and 25 μl of virus added in M-199 supplemented with 2% lamb serum. After 1 hour, 75 μL of medium containing test compound was added to each well containing virus. After 2–3 weeks incubation the cytopathic effect of the virus was determined by staining with a vital stain. Cell viability was measured by determining stain density using a 96 well plate reader.

Control wells without virus were completed to determine the toxicity of compounds.

Method B

Tissue culture plates were incubated at 37° C. in a humidified, 5% CO$_2$ atmosphere and observed microscopically for toxicity and/or cytopathogenic effect (CPE). At 1 hour prior to infection each test article was prepared from the frozen stock, and a 20 μl volume of each dilution (prepared as a 10× concentration) was added to the appropriate wells of both infected and uninfected cells.

Assays were done in 96-well tissue culture plates. CEM cells were treated with polybrene at a concentration of 2 μg/ml, and an 80 μl volume of cells (1×10$^4$ cells) was dispensed into each well. A 100 μl volume of each test article dilution (prepared as a 2× concentration) was added to 5 wells of cells, and the cells were incubated at 37° C. for 1 hour. A frozen culture of HIV-1, strain HTVL-IIIB, was diluted in culture medium to a concentration of 5×10$^4$ TCID$_{50}$ per ml, and a 20 μl volume (containing 10$^3$ TCID$_{50}$ of virus) was added to 3 of the wells for each test article concentration. This resulted in a multiplicity of infection of 0.1 for the HIV-1 infected samples. A 20 μl volume of normal culture medium was added to the remaining wells to allow evaluation of cytotoxicity. Each plate contained 6 wells of untreated, uninfected, cell control samples and 6 wells of untreated, infected, virus control samples.

On the 9th day post-infection, the cells in each well were resuspended and a 100 μl sample of each cell suspension was removed for use in an MTT assay. A 20 μl volume of a 5 mg/ml solution of 3-(4,5-dimethylthiazol-2-yl)-2,5-diphenyltetrazolium bromide (MTT) was add each 100 μl cell suspension, and the cells were incubated at 37° C. in 5% CO$_2$ for 4 hours. During this incubation MTT is metabolically reduced by living cells, resulting in the production of a colored formazan product. A 100 μl volume of a solution of 10% sodium dodecyl sulfate in 0.01N hydrochloric acid was added to each sample, and the samples were incubated overnight. The absorbance at 590 nm was determined for each sample using a Molecular Devices V$_{max}$ microplate reader. This assay detects drug-induced suppression of viral CPE, as well as drug cytotoxicity, by measuring the generation of MTT-formazan by surviving cells.

Tables 1 and 2, below, set forth the results of the foregoing assays for visna virus inhibition and HIV inhibition, respectively, by illustrative compounds prepared in the foregoing Examples.

TABLE 1

A. % INHIBITION OF VISNA VIRUS GROWTH AT VARIOUS CONCENTRATIONS (mM)

| Example No. Compound | 1.0 | 0.1 | 0.01 | 0.001 |
|---|---|---|---|---|
| 27 | 99 | 38 | 39 | |
| 28 | 100 | 100 | 61 | 6 |
| 29 | | 100 | 53 | 23 |
| 30 | 100 | 97 | 57 | 20 |
| 35 | | 41 | 31 | |
| 36 | 21 | | | |
| 34 | 100 | 89 | 7 | −2 |
| 40 | | 77 | 24 | 0 |
| 45 | 85 | 44 | 5 | |
| 32 | | 28 | −3 | 12 |
| 38 | 97 | 86 | 61 | |

TABLE 1-continued

B. % INHIBITION OF VISNA VIRUS GROWTH AT VARIOUS CONCENTRATIONS (mM)

| Example No. Compound | 0.05 | 0.005 | 0.0005 |
|---|---|---|---|
| 39 | 98 | 58 | 44 |

TABLE 2

ANTI-HIV ACTIVITY - % INHIBITION OF VIRUS INDUCED CYTOPATHIC EFFECT

| Example No. Compound | Inhibition |
|---|---|
| 27 | $EC_{50}$ = 43 μg/mL |
| 28 | $EC_{50}$ = 11 μg/mL |
| 47 | 36% @ 500 μg/mL |

EXAMPLE 63

Various compounds as prepared above were tested for enzyme inhibitory activity against alpha- and beta-glucosidase enzymes as follows:

ASSAYS FOR ALPHA-GLUCOSIDASE (YEAST) AND BETA-GLUCOSIDASE (ALMONDS)

Yeast alpha-glucosidase and almond beta-glucosidase activities were measured by a modification of the method of Evans, et al., *Phytochemistry* 22, 768–770 (1983). The modifications included (1) assay of activities at pH 7.4 in HEPES (N-2-hydroxyethylpiperazine-N'-2-ethanesulfonic acid) buffer, (2) measurement in 96 well microtiter plates and (3) inclusion of 10% DMSO in control and test samples.

The release of p-nitrophenol from the substrate p-nitrophenylglycoside was measured spectrophotometrically in the presence and absence of test compound. Each assay included a known inhibitor of the enzyme as a standard. $IC_{50}$ values were determined for compounds which inhibited the enzymes more than 50% at a 1 millimolar concentration.

Alpha-Glucosidase Inhibition Assay, pH 7.4

To 100 μl 50 mM HEPES buffer, pH 7.4, in a microtiter plate, add 20 μl test compound in DMSO (DMSO alone in control), 40 μl (0.013 units) yeast alphaglucosidase (Sigma) in HEPES buffer and pre-incubate at room temperature for 15 minutes. Add 40 μl 1.25 mM p-nitrophenyl-alpha-D-glucopyranoside (Sigma) in HEPES buffer, as substrate, and monitor absorbance change at 405 nm in a Biotek EIA Autoreader. Absorption change was measured at 15 to 25 minutes (reaction was linear for at least 30 minutes). Each sample was tested in triplicate. $IC_{50}$ values were determined from the linear portion of the log concentration vs % inhibition curve obtained from a minimum of 3 points. Deoxynojirimycin was used as standard inhibitor.

Beta-Glucosidase Inhibition Assay, pH 7.4

To 100 μl 50 mM HEPES buffer, pH 7.4, in a microtiter plate, add 20 μl test compound in DMSO (DMSO alone in control), 40 μl (0.136 units) beta-glucosidase (Sigma) in HEPES buffer and pre-incubate at room temperature for 15 minutes. Add 40 μl 1.25 mM p-nitrophenyl-beta-D-glucopyranoside in HEPES buffer, as substrate and monitor absorbance change at 405 nm in a Biotek EIA Autoreader. Absorption change was measured at 15 to 25 minutes (reaction is linear for at least 30 minutes). Each sample was tested in triplicate. $IC_{50}$ values were determined from the linear portion of the log concentration vs % inhibition curve obtained from a minimum of 3 points. Castanospermine was used as standard inhibitor.

Beta-Glucosidase Inhibitor Assay, pH 4.8

To 100 μl 50 mM sodium citrate buffer, pH 4.8, in a microtiter plate, add 15 μl test compound in DMSO (DMSO alone in control), 20 μl (0.017 units) beta-glucosidase (Sigma) in citrate buffer and pre-incubate at room temperature for 15 minutes. Add 25 μl 2.50 mM p-nitrophenyl-beta-D-glucopyranoside in citrate buffer, as substrate. Incubate at room temperature 20 minutes (reaction is linear for at least 30 minutes). Add 50 μl 0.4M NaOHo Read absorption change at 405 nm in a Biotek EIA Autoreader. Each sample was tested in triplicate. $IC_{50}$ values were determined from the linear portion of the log concentration vs % inhibition curve obtained from a minimum of 3 points. Castanospermine was used as standard inhibitor.

The inhibitory activity against alpha- and beta-glucosidase enzymes by various compounds prepared above is shown in the following Table 3:

TABLE 3

Enzyme Inhibitory Activity

| Example No. Compound | Concentration μM | Percent Inhibition | |
|---|---|---|---|
| Part A, Inhibition of α-Glucosidase (yeast) at pH 7.4 | | | |
| 28 | 1 | 4 | |
|  | 10 | 37.6 | |
|  | 100 | 82.9 | |
|  | 1000 | 95.5 | |
| 29 | 1 | 11.5 | |
|  | 10 | 61.5 | |
|  | 100 | 91.8 | |
|  | 1000 | 102.2 | |
| 30 | 1 | 4.6 | |
|  | 10 | 46.4 | |
|  | 100 | 87.3 | |
|  | 1000 | 97.5 | |
| 36 | 100 | 11 | |
|  | 1000 | −6.8 | |
| 47 | 100 | 22.7 | |
|  | 1000 | 24.8 | |
| 48 | 100 | 24.6 | |
|  | 1000 | 60.9 | |
| 49 | 100 | −12.6 | |
|  | 1000 | −20.5 | |
| 51 | 100 | 27.1 | |
|  | 1000 | 39.3 | |
| 53 | 100 | 20.1 | |
|  | 1000 | −29.4 | |
| 54 | 100 | 23.5 | |
|  | 1000 | 22.6 | |
| 56(a) | 100 | 18.1 | |
|  | 1000 | −8.2 | |
| 56(b) | 100 | 15.6 | |
|  | 1000 | 15.7 | |
| 58 | 100 | 36.2 | |
|  | 1000 | 44 | |
| Part B, Inhibition of β-Glucosidase (almond) at pH 7.4 or 4.8 | | | |
| 28 | 100 | 62.9 | 43.7 |
|  | 1000 | 90 | 84 |
| 29 | 100 | 54.7 | 33.1 |
|  | 1000 | 91.9 | 52.8 |
| 30 | 100 | 66.2 | 47.6 |
|  | 1000 | 92.5 | 84.7 |
| 36 | 100 | −2.4 | 4.3 |
|  | 1000 | 0.3 | 3.1 |
| 47 | 100 | −4.1 | 11.2 |
|  | 1000 | 6.7 | 32.6 |
| 48 | 100 | 6.9 | 9.5 |
|  | 1000 | 43.1 | 27.9 |
| 49 | 100 | −5.3 | 10.9 |
|  | 1000 | 0.2 | 18.8 |
| 51 | 100 | −3.8 | 6 |

TABLE 3-continued

| Example No. Compound | Enzyme Inhibitory Activity | |
|---|---|---|
| | Concentration $\mu M$ | Percent Inhibition |
| | 1000 | 4.4 | 26 |
| 53 | 100 | −4.2 | 1.6 |
| | 1000 | −7.3 | 9.5 |
| 54 | 100 | −7.8 | 0.1 |
| | 1000 | −7.9 | 4.1 |
| 56(a) | 100 | −3.4 | −0.9 |
| | 1000 | −15.8 | 13.7 |
| 56(b) | 100 | −6 | 7.5 |
| | 1000 | 5.7 | 29.4 |
| 58 | 100 | −7.5 | 1.8 |
| | 1000 | 13.2 | 18.6 |

The antiviral agents described herein can be used for administration to a mammalian host infected with a virus, e.g. visna virus or the human immunodeficiency virus, by conventional means, preferably in formulations with pharmaceutically acceptable diluents and carriers. These agents can be used in the free amine form or in their salt form. Pharmaceutically acceptable salt derivatives are illustrated, for example, by the HCl salt. The amount of the active agent to be administered must be an effective amount, that is, an amount which is medically beneficial but does not present toxic effects which overweigh the advantages which accompany its use. It would be expected that the adult human dosage would normally range upward from about one mg/Kg/day of the active compound, e.g., from about one to about 100 mg/Kg/day. The preferable route of administration is orally in the form of capsules, tablets, syrups, elixirs and the like, although parenteral administration also can be used. Suitable formulations of the active compound in pharmaceutically acceptable diluents and carriers in therapeutic dosage from can be prepared by reference to general texts in the field such as, for example, *Remington's Pharmaceutical Sciences,* Ed. Arthur Osol, 16th ed., 1980, Mack Publishing Co., Easton, Pa.

Various other examples will be apparent to the person skilled in the art after reading the present disclosure without departing from the spirit and scope of the invention. It is intended that all such other examples be included within the scope of the appended claims.

What is claimed is:

1. A compound of the formula

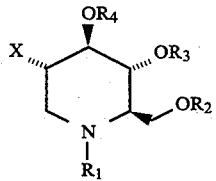

wherein X is Cl or Br; $R_1$ is H or a $C_1$–$C_{12}$ branched or unbranched alkyl group, alkoxyalkyl, alkenyl, alkynyl, arylalkyl, substituted arylalkyl, arylalkenyl, or substituted arylalkenyl; and $R_2$, $R_3$ and $R_4$ are independently H or $COR_5$ where $R_5$ is $C_1$–$C_6$ branched or unbranched alkyl, or $C_6$–$C_{12}$ aryl or alkylaryl.

2. A compound of claim 1 in which X is Cl.
3. A compound of claim 1 in which X is Br.
4. A compound of claim 1 in which $R_1$ is a $C_1$–$C_{12}$ alkyl group.
5. A compound of claim 4 in which the alkyl group is butyl.
6. A compound of claim 4 in which X is Cl.
7. A compound of claim 5 in which X is Cl.
8. A compound of claim 1 in which $R_2$, $R_3$ and $R_4$ are each H.
9. A compound of claim 2 in which $R_2$, $R_3$ and $R_4$ are each H.
10. A compound of claim 4 in which $R_2$, $R_3$ and $R_4$ are each H.
11. A compound of claim 5 in which $R_2$, $R_3$ and $R_4$ are each H.
12. A compound of claim 6 in which $R_2$, $R_3$ and $R_4$ are each H.
13. A compound of claim 7 in which $R_2$, $R_3$ and $R_4$ are each H.
14. A compound of claim 1 in which $R_2$, $R_3$ and $R_4$ are each $COR_5$ and in which $R_5$ is a $C_1$–$C_6$ alkyl group.
15. A compound of claim 2 in which $R_2$, $R_3$ and $R_4$ are each $COR_5$ and in which $R_5$ is a $C_1$–$C_6$ alkyl group.
16. A compound of claim 3 in which $R_2$, $R_3$ and $R_4$ are each $COR_5$ and in which $R_5$ is a $C_1$–$C_6$ alkyl group.
17. A compound of claim 4 in which $R_2$, $R_3$ and $R_4$ are each $COR_5$ and in which $R_5$ is a $C_1$–$C_6$ alkyl group.
18. A compound of claim 5 in which $R_2$, $R_3$ and $R_4$ are each $COR_5$ and in which $R_5$ is a $C_1$–$C_6$ alkyl group.
19. A compound of claim 6 in which $R_2$, $R_3$ and $R_4$ are each $COR_5$ and in which $R_5$ is a $C_1$–$C_6$ alkyl group.
20. A compound of claim 7 in which $R_2$, $R_3$ and $R_4$ are each $COR_5$ and in which $R_5$ is a $C_1$–$C_6$ alkyl group.
21. A compound of claim 9 in which $R_1$ is hexyl.
22. A compound of claim 9 in which $R_1$ is nonyl.
23. A compound of claim 9 in which $R_1$ is (3-phenyl)propyl.
24. A compound of claim 9 in which $R_1$ is (2-ethyl)butyl.
25. A compound of claim 9 in which $R_1$ is phenylmethyl.
26. A compound of claim 9 in which $R_1$ is (4-methoxyphenyl)methyl.
27. A compound of claim 20 in which $R_5$ is methyl.
28. A compound of claim 20 in which $R_5$ is propyl.
29. A compound of claim 18 in which $R_1$ is (3-phenyl)propyl and $R_5$ is methyl.
30. A compound of claim 16 in which $R_1$ is butyl and $R_5$ is methyl.
31. A compound of the formula

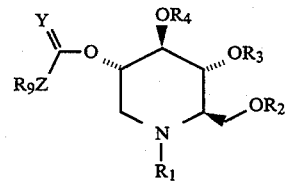

wherein Y is O or S; Z is NH or O; $R_1$ is H or a $C_1$–$C_{12}$ branched or unbranched alkyl group, alkoxyalkyl, alkenyl, alkynyl, arylalkyl, substituted arylalkyl, arylalkenyl, or substituted arylalkenyl; $R_2$, $R_3$ and $R_4$are independently H or $COR_5$; $R_5$ is a $C_1$–$C_6$ branched or unbranched alkyl, or $C_6$–$C_{12}$ aryl or alkylaryl; and $R_9$ is a $C_1$–$C_{12}$ branched or unbranched alkyl, or $C_6$–$C_{12}$ aryl or alkaryl.

32. A compound of claim 31 in which Y is O; Z is NH; $R_1$ is butyl; $R_2$, $R_3$ and $R_4$ are each H; and $R_9$ is butyl or phenyl.
33. A compound of claim 31 in which Y and Z are each O; $R_1$ is butyl; $R_2$, $R_3$ and $R_4$ are each H; and $R_9$ is methylpropyl.

* * * * *

UNITED STATES PATENT AND TRADEMARK OFFICE
CERTIFICATE OF CORRECTION

PATENT NO. : 5,451,679            Page 1 of 2
DATED : SEPT. 19, 1995
INVENTOR(S) : THOMAS E. BARTA and RICHARD A. MUELLER It is certified that error appears in the above-identified patent and that said Letters Patent is hereby corrected as shown below:

At col. 8, lines 1-10, the formula should appear as follows:

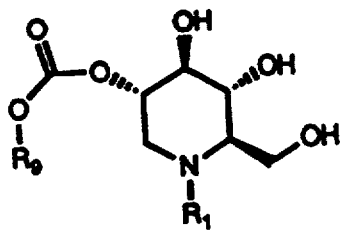

At col. 14, lines 60-67, delete the formula.

At col. 15, lines 5-12, the formula should appear as follows:

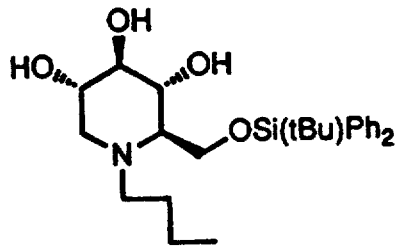

In each of the formulas at col. 15, lines 52-61, col. 16, lines 5-14, 27-36, and 50-58, and col. 17, lines 5-14 and 47-56, the floating OH should be shown as a substituent on the ring carbon at position number 2 (counting clockwise from the N) by broken lines to indicate stereochemical configuration as in the above-corrected formula at col. 15, lines 5-12.

UNITED STATES PATENT AND TRADEMARK OFFICE
CERTIFICATE OF CORRECTION

PATENT NO. : 5,451,679
DATED : SEPT. 19, 1995
INVENTOR(S) : THOMAS E. BARTA and RICHARD A. MUELLER It is certified that error appears in the above-identified patent and that said Letters Patent is hereby corrected as shown below:

In Claim 31, at col. 44, line 54, "Y is 0" should read

--Y is O -- and

"Z is NH or 0" should read

--Z is NH or O --

Signed and Sealed this

First Day of October, 1996

BRUCE LEHMAN

Commissioner of Patents and Trademarks